United States Patent [19]

Dunn

[11] Patent Number: 5,658,530
[45] Date of Patent: Aug. 19, 1997

[54] PHOTOCATALYST AND PULSED LIGHT SYNERGISM IN DEACTIVATION OF CONTAMINANTS

[75] Inventor: Joseph E. Dunn, Vista, Calif.

[73] Assignee: PurePulse Technologies, Inc., San Diego, Calif.

[21] Appl. No.: 626,976

[22] Filed: Apr. 3, 1996

Related U.S. Application Data

[63] Continuation of Ser. No. 483,818, Jun. 7, 1995, abandoned, which is a continuation-in-part of Ser. No. 312,697, Sep. 27, 1994, abandoned.

[51] Int. Cl.$^6$ .............................. A61L 2/00; B65B 55/00
[52] U.S. Cl. ............................... 422/24; 53/167; 53/426; 422/28; 422/292
[58] Field of Search ................. 422/22, 24, 28, 422/292; 53/167, 426, 141; 430/942; 426/248

[56] References Cited

U.S. PATENT DOCUMENTS

| | | | |
|---|---|---|---|
| 2,072,416 | 3/1937 | Berndt et al. | 99/13 |
| 2,072,417 | 3/1937 | Berndt et al. | 99/13 |
| 2,482,507 | 9/1949 | Rentschler et al. | 99/218 |
| 2,930,706 | 3/1960 | Moulton | 99/186 |
| 3,814,680 | 6/1974 | Wood | 210/64 |
| 3,817,703 | 6/1974 | Atwood | 21/2 |
| 3,934,044 | 1/1976 | Busch et al. | 426/326 |
| 3,955,921 | 5/1976 | Tensmeyer | 21/54 R |
| 3,994,686 | 11/1976 | Rauser et al. | 426/248 |
| 4,035,981 | 7/1977 | Braun et al. | 53/21 R |
| 4,042,325 | 8/1977 | Tensmeyer | 21/54 R |
| 4,265,747 | 5/1981 | Copa et al. | 210/758 |
| 4,391,080 | 7/1983 | Brody et al. | 53/426 |
| 4,396,582 | 8/1983 | Kodera | 422/300 |
| 4,424,188 | 1/1984 | DiGeronimo | 422/20 |
| 4,464,336 | 8/1984 | Hiramoto | 422/24 |
| 4,494,357 | 1/1985 | DiGeronimo | 53/167 |
| 4,861,484 | 8/1989 | Lichtin et al. | 210/638 |
| 4,871,559 | 10/1989 | Dunn et al. | 426/248 |
| 4,910,942 | 3/1990 | Dunn et al. | 53/425 |
| 5,035,235 | 7/1991 | Dunn et al. | 426/238 |
| 5,151,252 | 9/1992 | Mass | 422/186.3 |
| 5,433,738 | 7/1995 | Stinson | 422/24 |

FOREIGN PATENT DOCUMENTS

| | | |
|---|---|---|
| 0313409 | 4/1980 | European Pat. Off. |
| 7502834 | 3/1975 | Netherlands |
| 1052513 | 12/1963 | United Kingdom |
| 1346521 | 2/1974 | United Kingdom |
| 1448411 | 9/1976 | United Kingdom |
| 1548997 | 7/1979 | United Kingdom |
| 1581998 | 12/1989 | United Kingdom |

OTHER PUBLICATIONS

Johnson, "Flashblast—the light that cleans", *Popular Science*, pp. 82–84.

Rentschler, et al., "Bactericidal Effect of Ultraviolet Radiation", *Research Department, Westinghouse Lamp Division*, Bloomfield, New Jersey, pp. 745–774.

T. Saito, et al. "Mode of photocatalytic bactericidal action of powdered semiconductor TiO$_2$ on mutans streptococci" *J. Photochem. Photobiol. B: Biol.* vol. 14, pp. 369–379 (1992).

J. Sabate, et al. "A Kinetic Study of the Photocatalytic Degradation of 3-Chlorosalicylic Acid over TiO$_2$ Membranes Supported on Glass" *Journal of Catalysis* vol. 127, pp. 167–177 (1991).

(List continued on next page.)

*Primary Examiner*—George Yeung
*Attorney, Agent, or Firm*—Fitch, Even, Tabin & Flannery

[57] ABSTRACT

An improved method and apparatus for deactivating contaminants involves illuminating one portion of the contaminants with light having frequencies within a first prescribed frequency range, resulting in the deactivating of the one portion of the contaminants, and illuminating another portion of the contaminants with light having frequencies within a second prescribed frequency range, the other portion being at a titanium dioxide supplemented surface, so as to initiate the release of a highly reactive agent in a reaction in which titanium dioxide serves as a catalyst. The highly reactive agent deactivates the other portion of the contaminants.

21 Claims, 12 Drawing Sheets

OTHER PUBLICATIONS

Max Glaskin "Kill the bugs to cure the building" *New Scientist* pp. 22 (Mar. 1995).

John C. Ireland "Inactivation of *Escherichia coli* by Titanium Dioxide Photocatalytic Oxidation" *Applied and Environmental Microbiology* vol. 59, No. 5, pp. 1668–1670.

"Using Photocatalysts, Japanese Firm Develops Antibacterial Tiles and Sanitary Ware" 2 pgs.

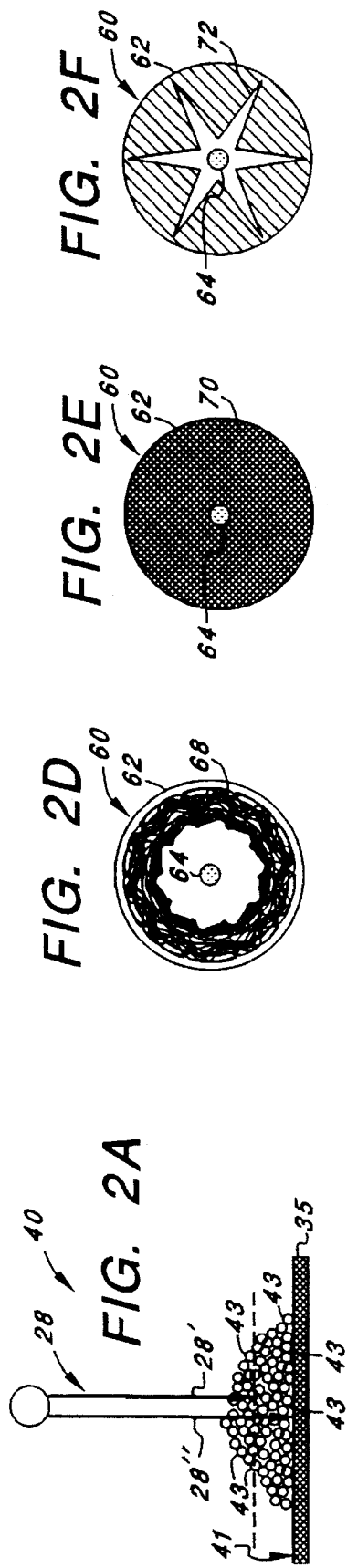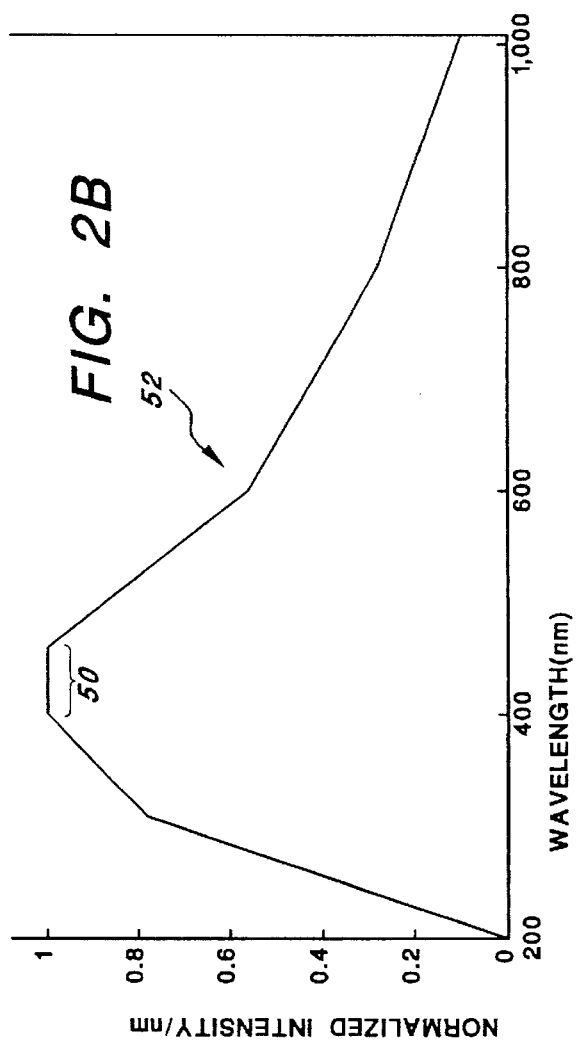

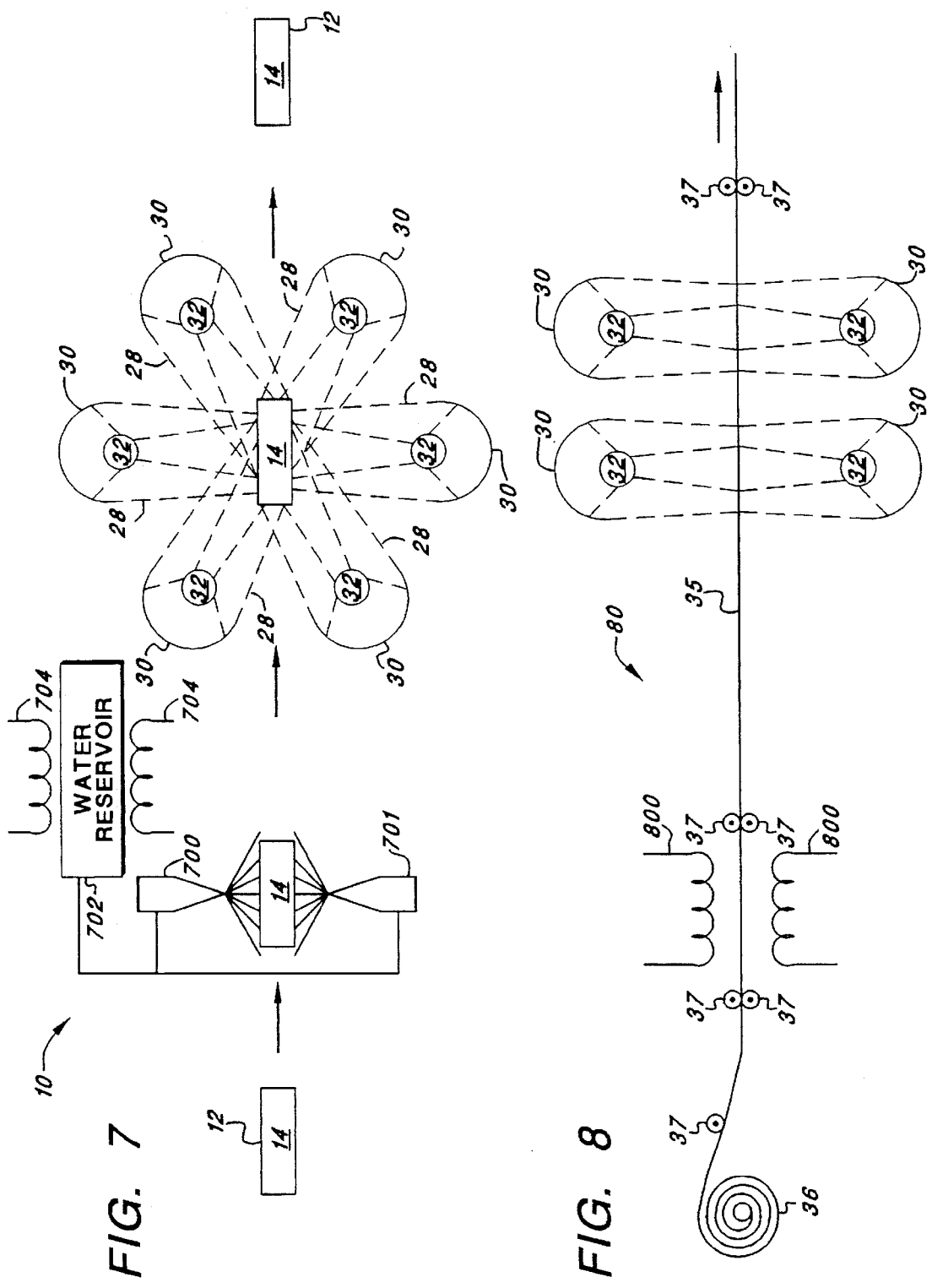

PHOTOCATALYST AND PULSED LIGHT SYNERGISM IN DEACTIVATION OF CONTAMINANTS

This application is a continuation of application Ser. No. 08/483,818 filed on Jun. 7, 1995, now abandoned, which is a continuation-in-part of U.S. patent application Ser. No. 08/312,697, filed Sep. 27, 1994, for SYNERGISM IN PULSED LIGHT TREATMENT OF FOOD PRODUCTS AND PACKAGING MATERIALS, incorporated herein by reference, now abandoned.

BACKGROUND OF THE INVENTION

The present invention relates to improved systems and methods for the deactivation of contaminants, i.e., organisms (biological contaminants) or chemical contaminants.

Fresh meats, fruits, vegetables, and other food products, for example beef carcasses, accumulate organisms, which as used herein includes bacteria, viruses, and fungi, from the air, ground, water and other sources with which they come into contact. These organisms, through various known mechanisms, cause the perishable food products to spoil, thereby significantly limiting the shelf-life of the food products. (Shelf-life is the period of time during which the perishable food product can be stored refrigerated or unrefrigerated, and remain edible and free from noticeable or harmful degradation or contamination by organisms.) As a result, methods and apparatuses suitable for deactivating, i.e., killing or sterilizing, such organisms and thereby extending the shelf-life of perishable foods, such as meats and other edible food products, are desirable.

The photobiological effects of light, including infrared light (780 nm to 2600 nm; i.e., $3.9 \times 10^{14}$ Hz to $1.2 \times 10^{14}$ Hz), visible light (380 to 780 nm; i.e., $7.9 \times 10^{14}$ Hz to $3.9 \times 10^{14}$ Hz), near ultraviolet light (300 to 380 nm; i.e., $1.0 \times 10^{15}$ Hz to $7.9 \times 10^{14}$ Hz) and far ultraviolet light (170 to 300 nm; i.e., $1.8 \times 10^{15}$ Hz to $1.0 \times 10^{15}$ Hz), have been studied, and efforts have been made to employ light to deactivate organisms on food products and packaging materials for food products. See, e.g., U.S. Pat. No. 4,871,559, issued to Dunn et al. (the '559 patent), incorporated herein by reference. Systems and methods employing the photobiological effects of light to deactivate, i.e., kill or sterilize, substantially all (i.e., more than 50%, e.g., 90%, deactivation rate) of the organisms on the surface of the food product and/or packaging material have proven to be effective in extending the shelf-life of perishable food products.

One improvement to systems that utilize the photobiological effects of light to effect deactivation of organisms on food products or food packaging materials is to treat the food product or food packaging material with an absorption enhancing agent prior to the illumination of the food product or packaging material. See e.g., the '559 patent. Absorption enhancing agents have a high optical absorption coefficient at least a portion of the spectral wavelengths with which the food product or packaging material is to be illuminated.

Another improvement to systems that utilize the photobiological effects of light to effect deactivation of organisms on food products is to subject the food product to a high pressure water wash prior to the illumination of the food product. See e.g., the '559 patent. The high pressure water wash physically removes some organisms from the surface of the food product prior to the illumination.

While these improvements to systems and methods that employ the photobiological effects of light to effect a prescribed level of deactivation of organisms on food products or food packaging materials are advantageous, further improvements in the deactivation rate, reduction of the time required to achieve a desired deactivation rate, and/or reduction of the energy needed to effect deactivation or kill are needed and highly desirable.

Photocatalytic effects have also been studied for bactericidal action. See Sabate, et al., "A Kinetic Study of the Photocatalytic Degradation of 3-Chlorosalicylic Acid over $TiO_2$ Membranes Supported on Glass", Journal of Catalysis, 127:167–177 (1991); Saito, et al., "Mode of Photocatalytic Bactericidal Action of Powdered Semiconductor $TiO_2$ on Mutans Streptococci", J. Photochem. Photobiol. B: Biol. 14:369–379 (1992); Ireland, et al., "Inactivation of *Escherichia Coli* by Titanium Dioxide Photocatalytic Oxidation", Applied and Environmental Microbiology, 59:5, pp. 1668–1670 (May 1993); Glaskin, "Kill the Bugs to Cure the Building", New Scientist, pp. 22 (Mar. 11, 1995); and "Using Photocatalysts, Japanese Firm Develops Antibacterial Tiles and Sanitary Ware", Tile Industry News, pp. 1, (May/June 1995), all of which are incorporated herein by reference.

Specifically, photocatalytic effects that result in the production of highly reactive agents (defined herein to mean superoxide ions and/or hydroxyl radicals ($HO^-$) (produced as a result of the cleavage of air or water)) have been the subject of research relating to the deactivation of contaminants, i.e., organisms (or biological contaminants) or chemical contaminants. This research has centered around the use of anatase titanium dioxide illuminated with light of wavelengths less than about 400 nm for extended periods of time (e.g., from several minutes to several days). Problematically, these highly reactive agents, i.e., the superoxide ions or hydroxyl radicals, are very short lived, due to their highly reactive nature. As a result, photocatalytic effects are effective in deactivating only contaminants located very near to, i.e., within an effective range of, the catalyst, i.e., titanium dioxide. Thus, while these studies have shown that photocatalytic effects offer some promise in the deactivation of contaminants, further improvements are needed to assure that contaminants located beyond the effective range of these effects are deactivated.

The present invention advantageously improves upon heretofore known systems and methods employing the photobiological effects of light, or, alternatively, photocatalytic effects, to deactivate contaminants.

SUMMARY OF THE INVENTION

The present invention advantageously addresses the needs above as well as other needs by providing an improved system and method for deactivating contaminants, i.e., biological or chemical contaminants on, e.g., a surface of a food product, on the surface of a packaging material, or in water or air. The invention advantageously employs heretofore unknown synergies that exist between pulsed light treatment, and thermal, chemical, modified atmosphere packaging or photocatalytic treatments.

In one embodiment, the invention can be characterized as an improved method for deactivating organisms on the surface of a perishable food product, or on the surface of a packaging material. Such method includes heating a surface of the food product, packaging material or atmosphere adjacent to such food product or packaging material to a prescribed temperature, and illuminating the surface of the food product, packaging material or adjacent atmosphere with light having frequencies within a prescribed frequency range. At least a portion of the light with which the food product or packaging material is illuminated deactivates organisms substantially at the surface of the food product or packaging material.

Such embodiment can also be characterized as a system for carrying out the above method. The system includes heating means for heating a surface of the food product, packaging material or adjacent atmosphere to a prescribed temperature, and illuminating means for illuminating the surface of the food product or packaging material with light. As above, the light has frequencies within a prescribed frequency range, and at least a portion of the light deactivates organisms substantially at the surface of the food product or packaging material.

In another embodiment, the invention can be characterized as a method for deactivating organisms substantially at a surface of a food product or packaging material including: applying a chemical agent to the surface of the food product or packaging material, and illuminating the surface of the food product or packaging material with light having frequencies within a prescribed frequency range. At least a portion of the light deactivates organisms substantially at the surface of the packaging material.

Such embodiment can also be characterized as a system for preserving a perishable food product or for deactivating organisms at a surface of a packaging material. The system includes: applying means for applying a chemical agent to a surface of the food product or packaging material, and illuminating means for illuminating the surface of the food product or packaging material with light. The light has frequencies within a prescribed frequency range, and at least a portion of the light deactivates organisms substantially at the surface of the food product or packaging material.

A further embodiment of the invention may be characterized as a method for preserving a perishable food product including: sealing the food product within a package designed to contain a modified atmosphere, and illuminating the package with light having frequencies within a prescribed frequency range. At least a portion of the light passes through the package and deactivates organisms substantially at the surface of the food product.

Such further embodiment may also be characterized as a system for preserving a perishable food product including: packaging means for sealing the food product within a package designed to contain a modified atmosphere, and illuminating means for illuminating the package with light having frequencies within a prescribed frequency range. As above, at least a portion of the light passes through the package and deactivates organisms substantially at the surface of the food product Even further embodiments of the invention employ a combination of one or more of the abovedescribed systems and methods, i.e., a combination of one or more of the above-mentioned synergies, in order to achieve improved deactivation of organisms at or near the surface of a food product or packaging material.

Another embodiment of the invention can be characterized as a method for deactivating contaminants, i.e., biological contaminants and/or chemical contaminants, substantially at a titanium dioxide supplemented surface of a packaging material. The method utilizes the steps of (a) illuminating the titanium dioxide supplemented surface with light having frequencies within a first prescribed frequency range, and (b) illuminating the titanium dioxide supplemented surface of the packaging material with light having frequencies within a second prescribed frequency range. At least a portion of the light having frequencies within the first frequency range deactivates contaminants substantially at the titanium dioxide supplemented surface of the packaging material, and at least a portion of the light having frequencies within the second frequency range initiates the release of a highly reactive agent in a reaction in which titanium dioxide serves as a catalyst. The highly reactive agent deactivates contaminants substantially at the titanium dioxide supplemented surface of the packaging material. Thus, in accordance with this embodiment, deactivation of the contaminants is achieved using two mechanisms: (a) photobiological or photochemical effects, which are in response to the light having frequencies in the first prescribed frequency range; and (b) photocatalytic effects, which are in response to light having frequencies in the second prescribed frequency range.

In an additional embodiment, also employing these two mechanisms, the invention can be characterized as a method for deactivating one or more contaminants within a treatment cell. This method employs the steps of (a) illuminating one portion of the contaminants with light having frequencies within a first prescribed frequency range, and (b) illuminating another portion of the one or more contaminants, at a titanium dioxide supplemented surface, with light having frequencies within a second prescribed frequency range. At least a portion of the light having frequencies within the first prescribed frequency range deactivates the one portion of the contaminants, and at least a portion of the light having frequencies within the second prescribed frequency range initiates the release of a highly reactive agent in a reaction in which titanium dioxide serves as a catalyst. As above, the highly reactive agent deactivates the other portion of the contaminants.

In a further additional embodiment, also employing the above two mechanisms, the invention can be characterized as an apparatus for deactivating one or more contaminants. The apparatus has a treatment cell, and an anatase titanium dioxide supplemented surface within the treatment cell. The anatase titanium dioxide surface may be, e.g., a part of the treatment cell, such as an inner surface of the treatment cell; a structure, such as a screen mesh, within the treatment cell; or may be a packaging material. A lamp assembly is positioned within the treatment cell that illuminates a portion of the contaminants with light having frequencies within a first prescribed frequency range. Means are provided as a part of the apparatus for illuminating another portion of the contaminants at the anatase titanium dioxide supplemented surface with light having frequencies within a second prescribed frequency range. Such means may, e.g., include the lamp assembly, may include sunlight, may include incandescent for florescent room lighting, or any other light source capable of initiating the release of highly reactive agents in a photocatalytic reaction with titanium dioxide. At least a portion of the light having frequencies within the first prescribed frequency range deactivates the one portion of the contaminants, and at least a portion of the light having frequencies within the second prescribed frequency range initiates the release of a highly reactive agent in a reaction in which titanium dioxide serves as a catalyst. The highly reactive agent deactivates the other portion of the contaminants.

It is therefore a feature of the invention to deactivate contaminants substantially at a titanium dioxide supplemented surface, and/or at a surface of a food product or food packaging material.

It is another feature of the invention to provide an improved pulsed light treatment system and method that employs thermal, chemical, modified atmosphere packaging and/or photocatalyst synergy (which is a form of chemical synergy).

BRIEF DESCRIPTION OF THE DRAWINGS

The above and other aspects, features and advantages of the present invention will be more apparent from the following more particular description thereof, presented in conjunction with the following drawings wherein:

FIG. 2A is a schematic diagram of a pulsed light treatment system employing a variation of chemical agent synergy to effect both photocatalytic and photobiological deactivation of contaminants at or near a surface of a packaging material;

FIG. 2B is a graph showing a light spectrum produced by a flashlamp system suitable for use with the pulsed light treatment system of FIG. 2A;

FIG. 2C is a side view showing a photocatalytic and photobiological treatment cell useable for the deactivation of contaminants in a gas or fluid;

FIG. 2D is a cross sectional view showing one embodiment of the treatment cell of FIG. 2C;

FIG. 2E is a cross sectional view showing an alternative embodiment of the treatment cell of FIG. 2C;

FIG. 2F is a cross sectional view showing a further embodiment of the treatment cell of FIG. 2C;

FIG. 7 is a schematic diagram of a pulsed light treatment system employing thermal synergy to achieve an improved organism deactivation rate substantially at a surface of a food product;

FIG. 8 is a schematic diagram of a pulsed light treatment system employing thermal synergy to achieve an improved organism deactivation rate substantially at a surface of a packaging material;

Corresponding reference characters indicate corresponding components throughout the several views of the drawings.

DETAILED DESCRIPTION OF THE INVENTION

The following description of the presently contemplated best mode of practicing the invention is not to be taken in a limiting sense, but is made merely for the purpose of describing the general principles of the invention. The scope of the invention should be determined with reference to the claims.

Figure 1:
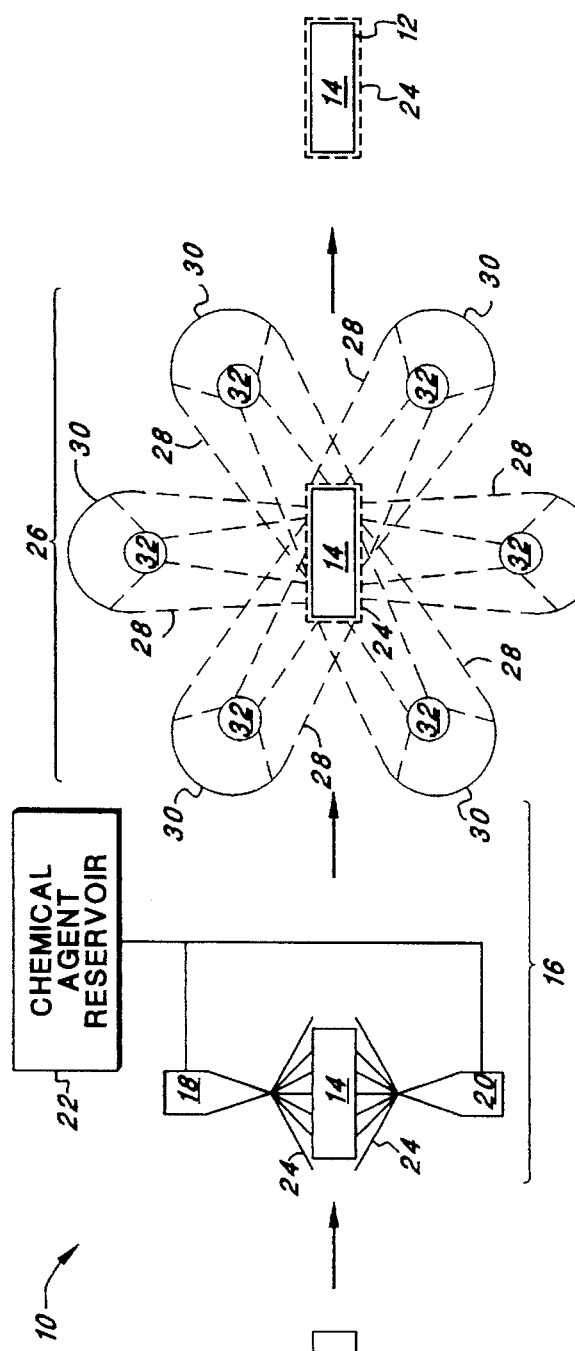
FIG. 1 is a schematic diagram of a pulsed light treatment system employing chemical agent synergy to achieve an improved biological contaminant (i.e., organism) deactivation rate substantially at a surface of a food product.

Referring first to FIG. 1, a schematic diagram is shown of a pulsed light treatment system 10 employing chemical agent synergy to achieve an improved organism deactivation rate substantially at (i.e., within one millimeter of) a surface 12 of a food product 14. The pulsed light treatment system 10 may be used to treat, i.e., deactivate organisms on, numerous types of food products including meats, produce, and prepared foods. Furthermore, the pulsed light treatment system 10 is effective in deactivating numerous type of organisms including *Escherichia coli* and *Salmonella typhimurium*.

In operation, for example, a meat product, such as steak, is passed, using e.g., a conveyor belt (not shown), into a chemical spray zone of a chemical agent applicator 16, such as a sprayer. The chemical agent applicator 16 includes, by way of example, two spray nozzles 18, 20 and a chemical agent reservoir. When the food product 14 passes into the chemical agent applicator 16, a chemical agent 24 is released from the chemical agent reservoir 22 by opening a valve (not shown). In response to the opening of the valve, the chemical agent flows to the nozzles 18, 20 and is sprayed onto the surface 12 of the food product 14.

Note that various other methods for applying the chemical agent, other than spraying, can be employed in addition to or instead of the sprayer. For example, the food product 14 (or, as described below, packaging material) may be dipped into a reservoir, or bath, of the chemical agent 24; the chemical agent 24 can be brushed onto the surface of the food product 14 (or packaging material); the chemical agent 24 may be rolled onto the food product 14 (or packaging material) using rollers; the food product (or packaging material) may be fogged with a aerated mist of the chemical agent 24; or the chemical agent 24 may be applied using any other suitable method for applying a liquid or gas to a solid. In a further variation, the chemical agent 24 may be in gaseous form and may be applied to the food product (or packaging material) using a gas jet or the like. The chemical agent 24 is applied to the food product 14 by the applicator until it substantially covers the outer surface 12 of the food product 14. Excess chemical agent 24 may optionally be removed from the outer surface 12 before the food product 14 is passed out of the applicator.

In practice, the chemical agent may include acids (inorganic or organic, such as acetic, lactic or citric acids), bases (inorganic or organic, such as alkaline aqueous solutions of sodium hydroxide or trisodium phosphate), detergents and other surfactants and surface active agents, natural byproducts or synthetic molecules with biological activity (such as antibiotics, bacteriocins, nicin, antibodies, chitin etc.), and/or enzymes (such as proteases, lysozymes, etc. or other enzymes with biological or antimicrobial activity). In addition, numerous other chemical agents that increase deactivation of organisms when combined with pulsed light treatment can be used. Alternatively, the chemical agent may consist of hot or warm water having a temperature of at least 20° C., e.g., 70° C.

As described more completely below, note that when hot or warm water is utilized as the chemical agent, both chemical synergy and thermal synergy, described hereinbelow, operate to improve the deactivation rate of organisms substantially at (i.e., within one millimeter of) the surface of the food product 14.

In one embodiment of the pulsed light treatment system 10 (as shown in FIG. 1), after application of the chemical agent 24 (and possibly heat, in the event hot or warm water is used as the chemical agent), the food product 14 is passed from the applicator 16 into a pulsed light treatment zone, wherein the food product 14 is exposed to intense (i.e., 0.01 to 50 $J/cm^2$, e.g., 0.5 $J/cm^2$, energy density measured at the surface of the food product), short duration (i.e., from 0.001 to 100 milliseconds, e.g., 0.3 milliseconds) pulses of polychromatic light 28 in a broad spectrum (i.e., 170 to 2600 nm; $1.8\times10^{15}$ Hz to $1.2\times10^{14}$ Hz). For example, the food product 14 can be exposed to four pulses (or flashes) of the polychromatic light.

In practice, the intense, short duration pulses of broad spectrum polychromatic light 28 are generated using a flashlamp system 30, such as PUREBRIGHT Model No. PL-320 available from PurePulse Technology of San Diego, Calif. The flashlamp system 30 includes a pulsing device (not shown) that includes a DC power supply that charges energy storage capacitors; a switch used to discharge the capacitors; a trigger circuit used to fire the switch at preprogrammed time intervals, in response to sensors that detect the position of the food product to be treated, or in response to a button being depressed; and a set of high voltage coaxial cables carrying the discharge pulses from a capacitor-switch assembly to a flashlamp assembly 26. The flashlamp assembly 26 includes from one to six flashlamps 32 mounted in metal reflectors 30 so as to direct the polychromatic light 28 emitted from the flashlamps 32 toward the food product 14.

One alternative system (not shown) utilizes a monochromatic light source, e.g., laser sources, that either pulses or continuously generates monochromatic light.

As a further alternative, the polychromatic lamp or the monochromatic source (that generates either coherent or incoherent monochromatic light) may be used to apply the polychromatic light, or the monochromatic light, respectively, for extended periods of time, i.e., for periods lasting more than one second, e.g., ten seconds or several minutes. The light of this alternative may be the broad spectrum polychromatic light of the preferred embodiment, or may be a narrower band of polychromatic light within the broad spectrum (170 nm to 2600 nm) defined above.

Thus, the light may also include continuous wave and monochromatic or polychromatic light having wavelengths outside the broad spectrum. However, at least 60%, preferably at least 70%, of the energy of the light should be from light having wavelengths within the broad spectrum defined above.

The pulses of polychromatic light are preferably from between 0.001 mS to 100 mS, e.g., 0.3 mS, in duration and have a pulse repetition rate of from one to 100 pulses, e.g., 10 pulses, per second (Hz). The food product 14 can be exposed to, e.g., four pulses (or flashes) of the polychromatic light 28.

In one alternative variation, the intense, short duration, pulses of broad spectrum, polychromatic light may be applied to the surface of the food product prior to application of the chemical agent thereto. Such can be achieved using an apparatus similar to the pulsed light treatment system shown in FIG. 1 with the chemical agent applicator 16 and flashlamp assembly 26 being in reversed positions.

In another alternative variation, the food product 14 is not passed to a treatment zone separate from the chemical spray zone. Instead, the chemical spray zone and the pulsed light treatment zone are combined. In operation, the pulsed light treatment system of this alternative variation first applies the chemical agent 24, and then applies the intense, short duration pulses of broad spectrum polychromatic light 28, or vice versa.

Illumination of the entire surface of the food product is preferred and can be achieved by rotating (e.g., using rollers or a shaker apparatus) the food product 14 between two or more flashes of a polychromatic lamp 32; by dropping the food product 14 within the treatment zone and exposing the food product 14 from all sides as it falls; by moving the food product 14 through the treatment zone on a transparent carrier, e.g., a transparent conveyor belt; or by manually (hand) rotating the food product in the treatment zone.

The pulses of light 28 impinge upon the surface 12 of the food product 14, so as to deactivate organisms at or near (i.e., within one millimeter of) the surface 12 of the food product 14. Such exposure, in combination with the application of the chemical agent 24 (and possibly heat), deactivates, i.e., kills or sterilizes, a substantial portion (i.e., more than 50%, e.g., 90%) of the organisms on the surface 12 of the food product 14.

In this way, improved deactivation of organisms substantially at the surface of the food product, i.e., an improved deactivation rate, is achieved.

Demonstration of the above-described chemical synergy is made by inoculating the surface of a beef carcass with 100 microliters *Escherichia coli* inoculum distributed as approximately ten small droplets across an 8 cm by 8 cm square area of the surface of the carcass. The inoculum is spread over the area using a bent glass rod and the organisms are allowed to attach for 30 minutes. Next, the area is sprayed for fifteen seconds using a 0.4 gallon per minute spray nozzle at 20 psi with a chemical agent consisting of 1.75% acetic acid in water. After a thirty second delay, the surface is treated with two flashes of broad spectrum, polychromatic light having a 0.3 mS pulse duration, a 1 pulse per second (Hz) repetition rate, and an energy density of 0.5 $J/cm^2$ measured at the surface of the carcass.

The area is next stomached (using a stomacher, which is a common laboratory device employing two paddles that pummel a sample within a bag containing a buffer, e.g., 100 ml of 0.1% peptone water, simulating processes carried out by a human stomach). The buffer is sampled and plated onto standard plate count agar (SPCA) plates and McConkey agar with Sorbitol (used as a selective and differential medium) (McC+S) plates. Standard microbiological techniques are then used to determine the logs of organisms still surviving. This quantity is compared to the logs of organisms measured on a control sample to determine the difference in logs of organisms, i.e., the increase in deactivation achieved by the combination of pulsed light treatment and the chemical agent. Results from an exemplary demonstration (including control samples and chemical-agent-only samples) are shown graphically in FIG. 1A.

Figure 1A:
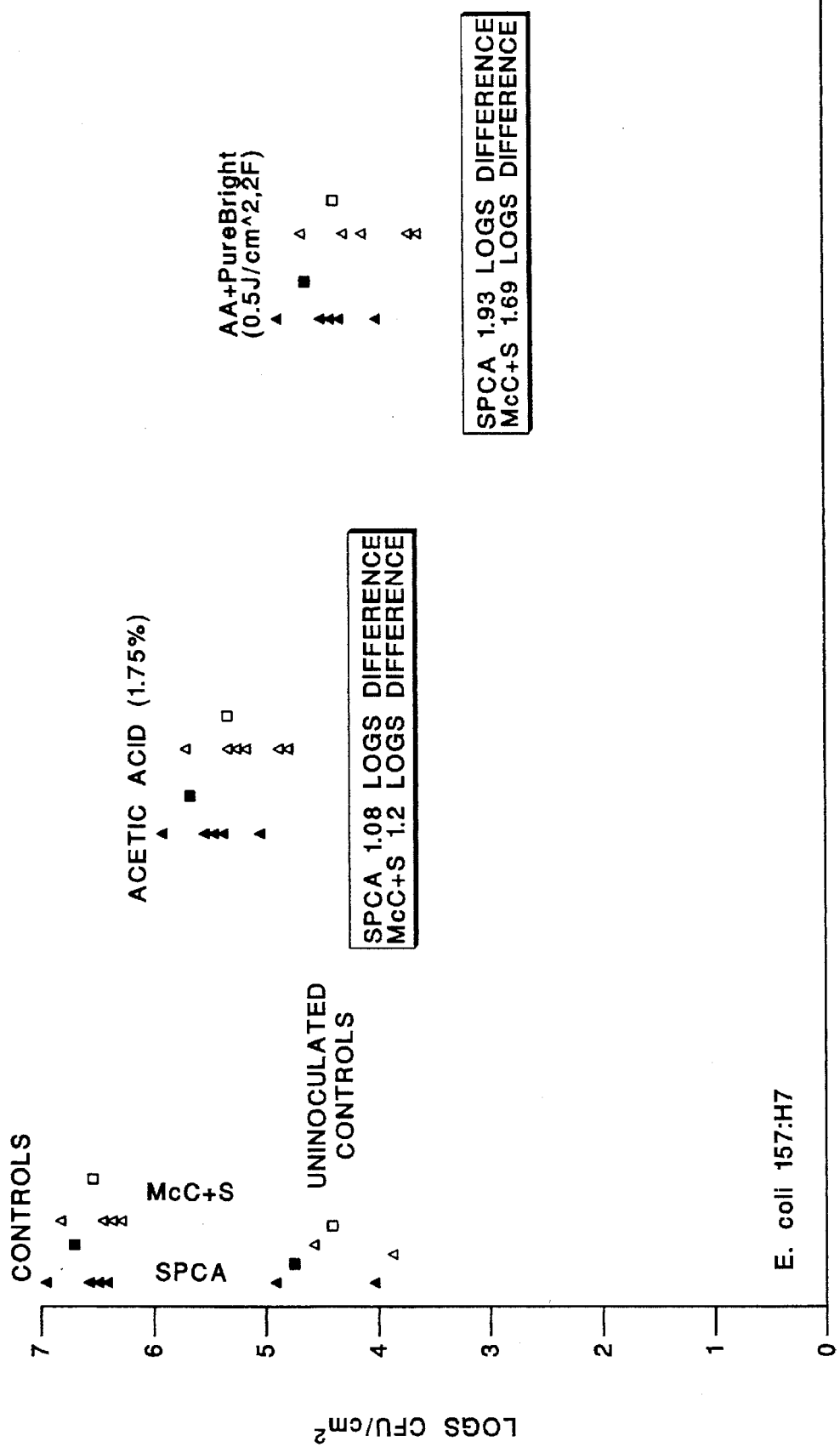
FIG. 1A is a graph showing results of a demonstration test of the pulsed light treatment system of FIG. 1 using *Escherichia coli* treated with acetic acid and two flashes of intense, short duration, broad spectrum, polychromatic light.

Referring to FIG. 1A, a graphical representation is shown of exemplary test results for the above demonstration. Organism levels are shown along a vertical axis (in logs CFU/cm$^2$) for three sets of test data. The first set is a control group (representing areas of the carcass that are inoculated with *Escherichia coli*, but not treated), the second is inoculated and treated only with acetic acid and the third (described above) is inoculated and treated with acetic acid and intense, short duration pulses of broad spectrum, polychromatic light. Each of the sets contains five samples plated on SPCA and five samples plated on McC+S agar (represented as closed and open triangles, respectively). Within each of the three groups, an average organism level is represented for SPCA and McC+S agar (as a closed and as an open square, respectively). Two additional control samples are taken on areas of the carcass that are not inoculated with *Escherichia coli* (referred to in FIG. 1A as "uninoculated controls"). Organism counts for such uninoculated control samples are plated on SPCA and McC+S agar (represented by closed and open triangles, respectively), and average organism counts are represented (by closed and open squares for SPCA and McC+S agar, respectively).

Figure 1B:
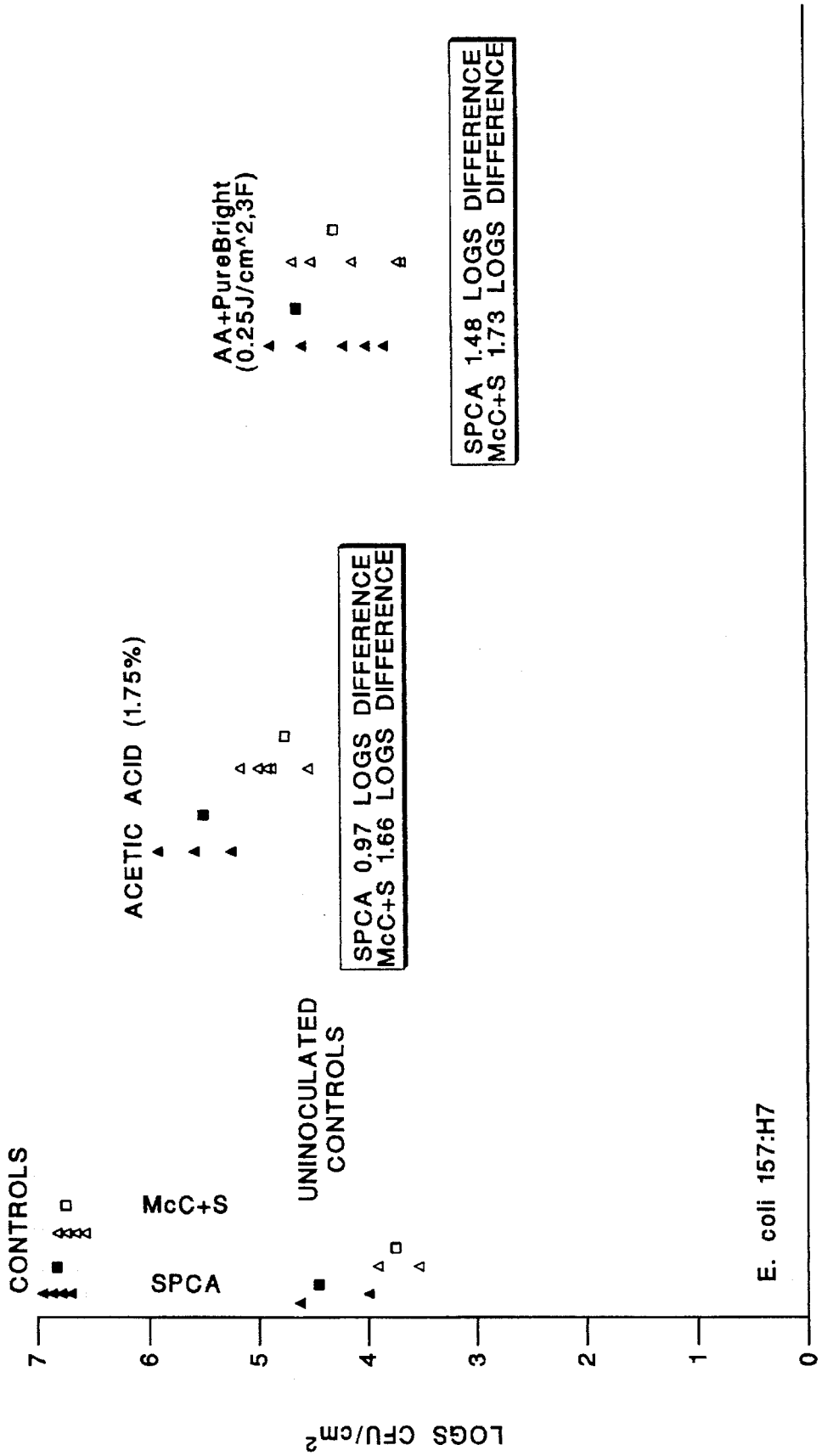
FIG. 1B is a graph showing results of another demonstration test of the pulsed light treatment system of FIG. 1 using *Escherichia coli* treated with acetic acid and three flashes of intense, short duration, broad spectrum, polychromatic light.

A similar demonstration of chemical synergy may also be performed using three, as opposed to two, intense, short duration pulses of broad spectrum polychromatic light. Results from such a demonstration are shown graphically in FIG. 1B. Test data for three groups of samples is represented in FIG. 1B in a manner similar to such representations in FIG. 1A.

Figure 1C:
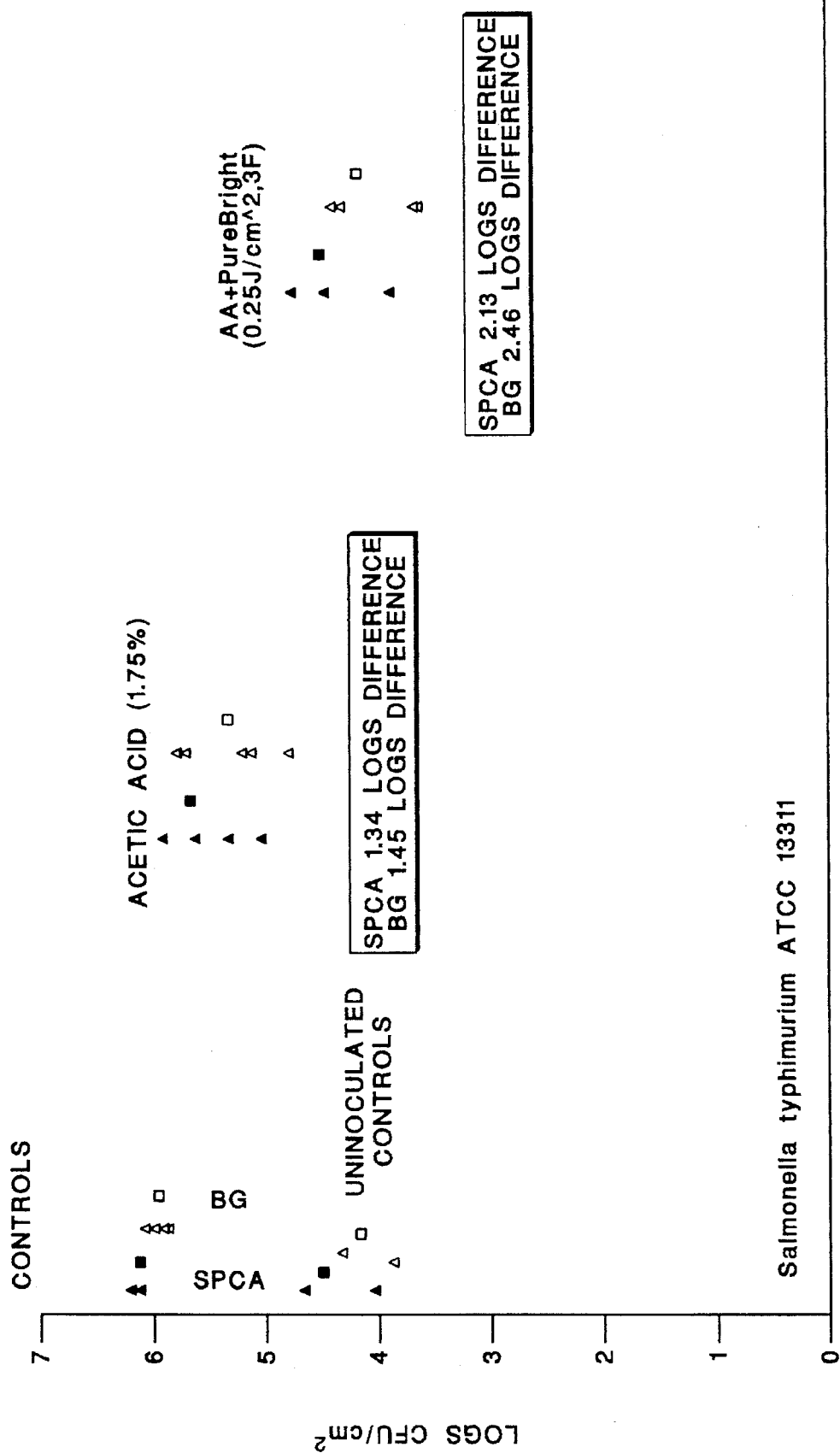
FIG. 1C is a graph showing results of a demonstration test of the pulsed light treatment system of FIG. 1 using *Salmonella typhimurium* treated with acetic acid and two flashes of intense, short duration, broad spectrum, polychromatic light.

Results from a demonstration using *Salmonella typhimurium* instead of *Escherichia coli*, and using three intense, short duration pulses of broad spectrum polychromatic light area shown graphically in FIG. 1C. Test data for three groups of samples is represented in FIG. 1C in a manner similar to such representations in FIG. 1A. Instead of McC+S agar and SPCA agar, brilliant green (BG) agar and SPCA agar are used in the *Salmonella typhimurium* demonstration.

Figure 2:
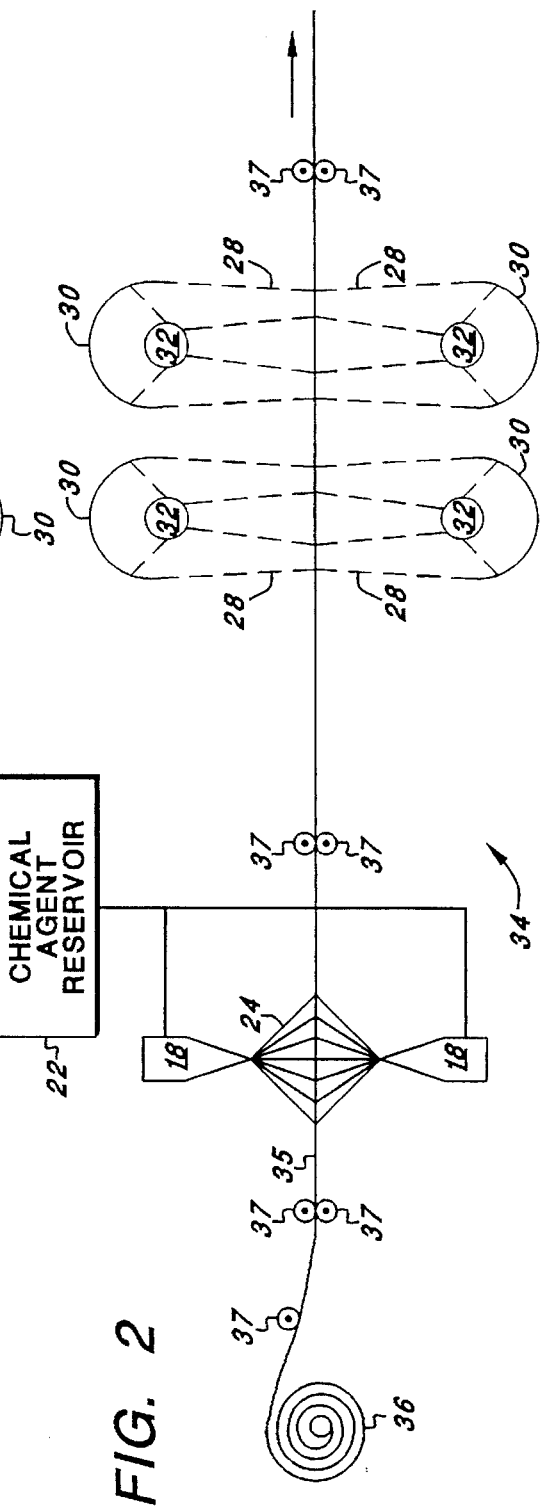
FIG. 2 is a schematic diagram of a pulsed light treatment system employing chemical agent synergy to achieve an improved organism deactivation rate substantially at a surface of a packaging material.

Referring to FIG. 2, a schematic diagram is shown of a pulsed light treatment system 34 employing chemical agent synergy to achieve an improved organism deactivation rate substantially at a surface of a packaging material 35. A roll 36 of packaging material 35, such as a laminate having an inner polyethylene layer, an aluminum foil layer, a paper layer, and an outer polyethylene layer, is shown. In practice, the packaging material 35 is passed through rollers 37 (or other appropriate mechanical guides) to a chemical agent spray zone, similar to that described above, wherein the chemical agent 24 is sprayed onto inner and outer surfaces of the packaging material 35 (or only one of the inner and outer surfaces, if desired). The packaging material 35 is then passed through additional rollers 37 (or mechanical guides) to a pulsed light treatment zone, wherein intense, short duration, broad spectrum, polychromatic light pulses 28 (described above) are applied to one or both surfaces of the packaging material 35.

It is important that the light pulses 28 be of high intensity, however the light pulses 28 should not be of such intensity that they cause the inner or outer surface of the packaging material 35, i.e., the inner or outer layer of polyethylene, to melt, burn or ablate from the foil or paper layers.

After application of the pulses of light 28, the packaging material 35 is passed through a final set of rollers 37 (or mechanical guides) and to a conventional food packaging apparatus (not shown). In passing the packaging material 35, having been treated, to the packaging apparatus, it is important that the surfaces of the packaging material 35 (i.e., the treated surfaces) remain sterile so as to prevent reinfestation of the surfaces with organisms. Such packaging apparatuses are well known in the art of food processing and could easily be adapted by one skilled in the art to function with the apparatus of FIG. 2.

Referring next to FIG. 2A, a schematic diagram is shown of a pulsed light treatment system 40 employing a variation of chemical agent synergy (referred to herein as a photocatalyst and pulsed light synergy) to effect both photocatalytic, and photobiological and/or photochemical deactivation of contaminants, (i.e., biological contaminants and chemical contaminants) at or near a surface 41 of a packaging material 35. A flashlamp 32 is shown, which may be part of a flashlamp assembly, such as is shown in FIG. 2. A colony 42 of contaminants, such as organisms 43 (i.e., biological contaminants), is depicted on the surface 41 of the packaging material 35.

The packaging material 35 may include the above-described laminate having an inner polyethylene layer, an aluminum foil layer, a paper layer, and an outer polyethylene layer. The surface 41 of the packaging material 35 on which organisms 43 are to be deactivated is generally the inner surface of the packaging material 35, i.e., the surface of the packaging material 35 against, or adjacent to, which food product is or will be packaged.

In accordance with the embodiment shown in FIG. 2A, the surface 41 is supplemented (e.g., coated, bonded or impregnated) with anatase titanium dioxide. Titanium dioxide, generally, is very well documented, and is stable and harmless if ingested by humans. In operation, intense (i.e., 0.01 to 50 J/cm$^2$, e.g., 0.5 J/cm$^2$, energy density measured at the surface of the packaging material), short duration (i.e., from 0.001 to 100 milliseconds, e.g., 0.3 milliseconds) pulses of polychromatic light 28 in a broad spectrum (i.e., 170 to 2600 nm; $1.8 \times 10^{15}$ Hz to $1.2 \times 10^{14}$ Hz) are directed to the anatase titanium dioxide supplemented surface 41 of the packaging material 35. One portion of the light 28', having wavelengths smaller than about 300 nm, e.g., from about 200 nm to 320 nm, impinges on the colony 42, but may not pass completely through the colony to the surface 41 of the packaging material, due to the thickness and the absorbativeness (at wavelengths below about 300 nm) of most biological cells, molds, bacteria and viruses, due to their high content of aromatic conjugated carbon systems in their proteins and nucleic acids. Another portion of the light 28", having wavelengths in the range of from about 300 nm to about 415 nm, passes through the colony 42 to the surface of the packaging material 35, due to the relatively low absorbativeness of most biological cells, molds, bacteria and viruses at wavelengths above about 300 nm.

The one portion 28' of the light 28 is predominantly responsible for causing photobiological deactivation of organisms 43 within the colony 42. Because the one portion 28' may be largely or entirely absorbed by organisms 43 near the surface of the colony 42, such deactivation may, in relatively thick colonies 42 of some types of organisms, occur only near the surface of the colony 42.

The other portion 28" of the light 28, while less effective, or ineffective, at causing photobiological deactivation of organisms, initiates the photocatalytic reaction at the anatase titanium dioxide supplemented surface 41 of the packaging material 35. The photocatalytic reaction includes the generation of, e.g., hydroxyl radicals, which are highly reactive. Because the hydroxyl radicals have a relatively short half life, they react with, and cause the deactivation of, organisms 43 lying near, i.e., local to, the surface 41 of the packaging material 35. In other words, organisms that may not be reached by the one portion 28' of the light 28, and therefore subjected to photobiological and/or photochemical effects, are more likely to be reached by the other portion 28" of the light 28, and therefore subjected to photocatalytic effects. Thus, photobiological and/or photochemical effects and photocatalytic effects work synergistically to deactivate organisms 43 (or other contaminants, e.g., chemical contaminants) both near the surface of the colony 42, and near the surface 41 of the packaging material 35, i.e., away from the surface of the colony 42.

When the colony 42 is particularly thick, the portions 28', 28" of the light 28, respectively, cause photobiological and/or photochemical effects, predominantly near the surface of the colony 42, and photocatalytic effects, predominantly near the surface 41 of the packaging material 35. Together, these two effects, i.e., photobiological and/or photochemical, and photocatalytic effects, cause deactivation of the organisms 43 (and/or photochemical and photocatalytic effects cause the deactivation of other contaminants, such as chemical contaminants), within the colony 42. The deactivation achieved by through these effects is potentially superior to that achieved by any one of these effects alone.

While the embodiment of FIG. 2A preferably utilizes the same intense, short duration, broad spectrum pulses of polychromatic light 28, having the one and the other portions 28', 28", to generate both photobiological and/or photochemical, and photocatalytic effects, it is envisioned that the pulse(s) of light used to generate photobiological and/or photochemical effects may be applied before application of the pulse(s) of light used to generate photocatalytic effects, or vice versa. These separate pulses of light may also be interleaved with one another, if multiple pulses of light are used to generate either photobiological or photocatalytic effects, or both.

It is further envisioned that the pulse(s) of light used to generate photobiological effects may be applied from a separate light source than that used to generate the pulse(s) of light that generate photocatalytic effects. Such separate light sources may include the flashlamp system described herein and/or, for example, continuous wave sources, fluorescent lights and/or sunlight. It is also envisioned that the light sources may be in separate "photocatalytic effect" and "photobiological effect" zones, just as the chemical spray zone and the pulsed light treatment zone, described above in reference to FIG. 2, are physically separate zones. The packaging material may be moved from one zone to the other zone using a conveyor similar to that described in reference to FIG. 2.

In one particular embodiment in which separate treatment zones are employed, the packaging material is an anatase titanium dioxide supplemented, e.g., impregnated, transparent or semi-transparent package, such as a food cup, as is commonly used to package pudding or yogurt. In practice, the package is first treated (i.e., illuminated with) with one or more short duration pulses of intense, broad spectrum, polychromatic light, so as to deactivate contaminants in the packaging through photobiological, photochemical and/or photocatalytic effects. Next, the package is filled with the food product, e.g., pudding, and sealed with, e.g., a foil laminate top. When the package and food product are placed on the shelf at, e.g., a supermarket, they are exposed to ambient light, which includes light having wavelengths in the range of from between 300 nm to 415 nm. The ambient light, which may come, for example, from sunlight or fluorescent lighting, along with the anatase titanium dioxide in the packaging material, is capable of causing the photocatalytic generation of highly reactive agents, e.g., superoxide ions and/or hydroxyl radicals, which in turn deactivate contaminants near the surface of the package. Advantageously, because the package is transparent or semi-transparent, the ambient light passes through the package and causes the generation of photocatalytic effects on the inner surface of the package.

Thus, the illumination of the package with one or more pulses of light, before the food product is packaged, causes the deactivation of contaminants on the surface of the package prior to the food product being packaged, and the combination of the ambient light and the anatase titanium dioxide in the packaging material provide for ongoing decontamination of the packaging material's surface when the package is exposed to ambient light. The above-described particular embodiment thus provides, through the use of a synergistic combination of photobiological and/or photochemical effects, and photocatalytic effects, an improved mechanism for the deactivation of contaminants. The packaging apparatuses shown in FIGS. 5 and 6, described hereinbelow, are suitable for carrying out this embodiment.

Referring back to the embodiment of FIG. 2A, both portions 28', 28" of the intense, broad spectrum, polychromatic light 28 are preferably applied in a single short duration pulse, from the same light source(s), e.g., flashlamp(s), in the same treatment zone. The light 28, preferably contains wavelengths from 200 nm to 1 μm, with peak intensity 50 (FIG. 2B) at wavelengths of 400 nm to 450 nm. A graph is shown in FIG. 2B of a light spectrum 52 produced by a preferred flashlamp system suitable for use with the pulsed light treatment system of the present embodiment. The preferred flashlamp system, which is described in more detail herein, is available as PUREBRIGHT Model No. PL-320 available from PurePulse Technology of San Diego, Calif., and may be used to generate the light spectrum shown in FIG. 2B.

While the present embodiment has been described as operating on the colony 42 of organisms 43 on a packaging material surface 41, it is envisioned that the present embodiment can be adapted to deactivate contaminants, i.e., biological contaminants and/or chemical contaminants, on any surface that can be supplemented (e.g., coated, bonded or impregnated) with anatase titanium dioxide, and that can be illuminated with light capable of generating photobiological or photochemical effects and, in combination with the anatase titanium dioxide, generating photocatalytic effects. For example, biofilms on filters, made to incorporate anatase titanium dioxide, can be treated with intense, short duration, broad spectrum pulses of polychromatic light so as to cause photobiological, photochemical and photocatalytic effects, as described herein, thereby causing the deactivation of contaminants passing through the filters.

In an alternative embodiment, gases and fluids, e.g., air and water, can be decontaminated by deactivating some or all of the contaminants (i.e., biological agents contaminants (including organisms) and/or chemical contaminants) present in the gases and fluids. Photobiological, photochemical and photocatalytic effects resulting from the pulses of light and, in the case of photocatalytic effects, the titanium dioxide, serve to deactivate a wide range of contaminants.

Referring to FIG. 2C, a side view is shown of a photocatalytic, and photobiological and/or photochemical treatment cell 60. The cell 60 includes an outer tube 62, which may or may not be impregnated with anatase titanium dioxide, and a coaxial flashlamp 64. Numerous cell geometries are contemplated, however, the illustrated coaxial cell 60 offers the advantage of relatively uniform light dispersion, and uniform flow characteristics. In practice, gas or liquid is passed through the outer tube 62, which may be made from, e.g., quartz, stainless steel or aluminum, using, e.g., a blower or vacuum, or a pump (not shown), such as is well known in the art. The direction of flow of the gas or liquid is represented in FIG. 2C using large arrows and dashed lines.

FIG. 2D shows a cross sectional view of one embodiment of the treatment cell 60 employing a porus mass 68 of anatase titanium dioxide impregnated material through which the gas or liquid passes as it passes through the outer tube 62. The porus mass may consist of fibers, filters, wires, beads, particles or matrixes of anatase titanium dioxide supplemented material, or of pure anatase titanium dioxide. As the gas or liquid passes through the porus mass 68, which may include, e.g., stainless steel or aluminum fibers, glass beads (packed within the outer tube) or a water-permeable gelatinous mass, the flashlamp 64 is used to generate one or more, e.g., four, short duration pulses of intense, broad spectrum polychromatic light. The light operates on contaminants within the gas or liquid, as described above, to deactivate the contaminants both through photobiological and/or photochemical effects and photocatalytic effects.

Advantageously, the photocatalytic effects, and in some cases the pulses of polychromatic light themselves (through photochemical effects), may be employed to effect chemical changes in the gas or liquid, thereby causing the deactivation of chemical contaminants, in addition to or instead of the deactivation of biological contaminants. For example, harmful chemical contaminants, such as nerve gas agents, toxins, allergens, air pollution agents, e.g., $NO_x$, $SO_x$, acid rain, etc., aflotoxins and/or mycotoxins, may be deactivated and neutralized. When the threat of chemical or biological warfare agents in air or water is present, a combination of photobiological, photochemical, and photocatalytic effects, as described herein, can be used to ensure high levels of organism (i.e., biological contaminant) deactivation, and, simultaneously, to ensure deactivation of chemical contaminants. Thus, the embodiment shown in FIGS. 2C and 2D (or alternatively, as described below, in FIGS. 2C and 2E, or FIGS. 2C and 2F), advantageously provides effective, broad range, high level decontamination of both organisms and chemical contaminants.

Referring to FIG. 2E, a cross sectional view is shown of an alternative embodiment of the treatment cell 60 of FIG. 2C employing a screen mesh 70, which may include, e.g., stainless steel, plastic, paper, filters or cellulose, impregnated with anatase titanium dioxide, through which the gas or liquid passes as it passes through the outer tube 62. In practice, several screens may be positioned, e.g., normal to a central axis of the outer tube 62, along the length of the treatment cell 60. At the center of the tube 62 is located the coaxial flashlamp 64, as shown in FIG. 2C.

Referring next to FIG. 2F, a cross sectional view is shown of a further embodiment of the treatment cell 60 of FIG. 2C employing a tube having an anatase titanium dioxide supplemented star-shaped cross section at its interior (star-shaped interior). The star-shaped interior 72 is designed to maximize the interior surface area of the tube, thereby maximizing contact between the gas or fluid being treated and the anatase titanium dioxide supplemented interior. Numerous other embodiments, employing numerous other interior surface geometries, are envisioned that utilize a maximized interior surface area to achieve this purpose. At the center of the star-shaped interior 72 is located the coaxial flashlamp 64, as shown in FIG. 2C.

Other embodiments of the treatment cell 60 shown in FIG. 2C employ wires (positioned either parallel to the central axis or otherwise), and/or particles (which may be gas-born or held within, for example, a filter) containing anatase titanium dioxide. The wires and/or particles are located within the outer tube, as with the porous mass 60 (FIG. 2D), the mesh screen 62 (FIG. 2E), and the star-shaped interior 72 (FIG. 2F). The coaxial flashlamp 64 is positioned at the center of the tube, as in FIG. 2C.

Figure 3:
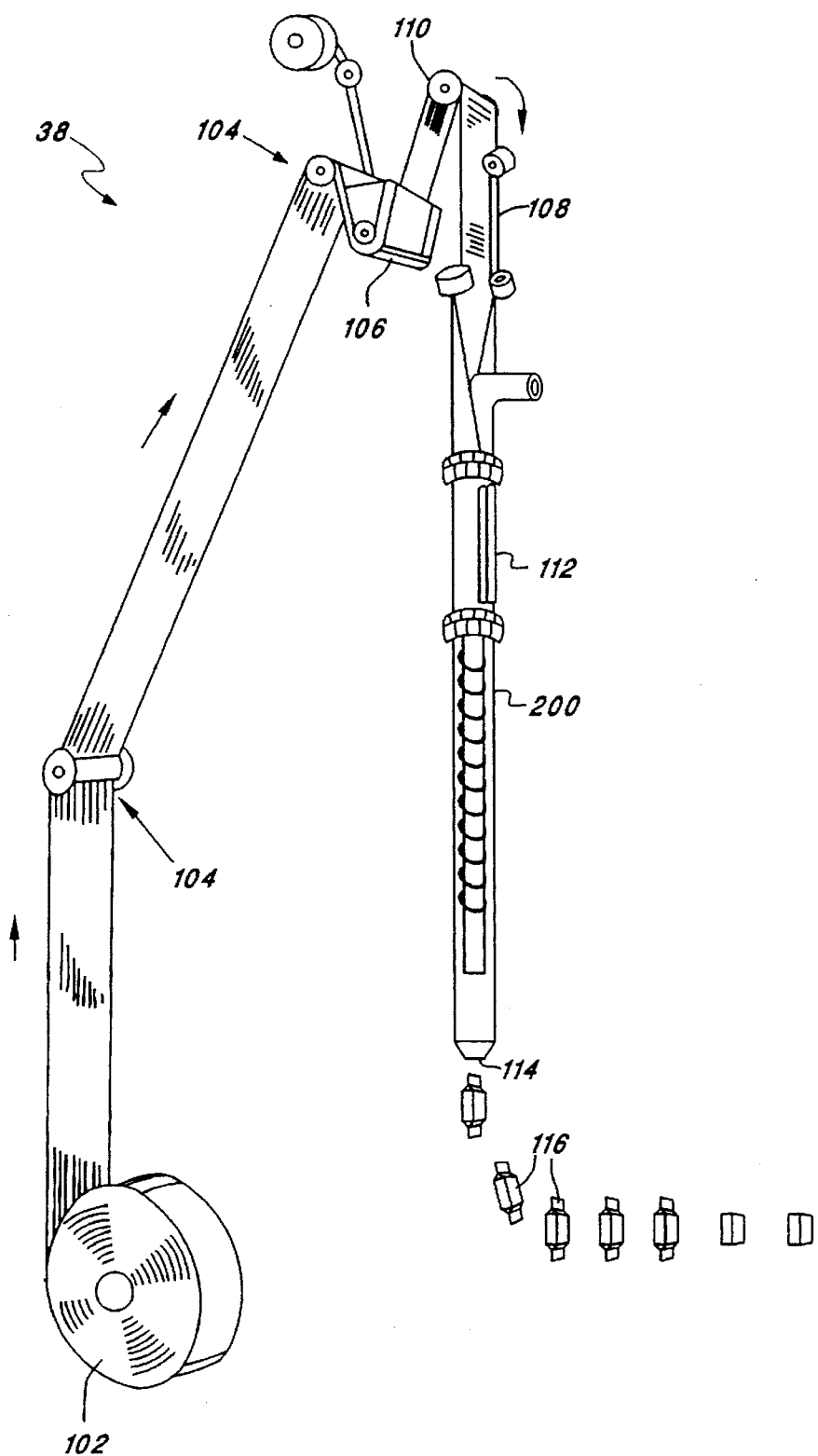
FIG. 3 is a detailed perspective view of a first type of aseptic packaging apparatus that includes an embodiment of the pulsed light treatment system of FIG. 2 employing chemical agent synergy.

Referring to FIG. 3, a detailed perspective view is shown of a first type of aseptic packaging apparatus 38. A roll or reel of packaging material 102 is directed by means of a series of rollers 104 through a reservoir 106 (i.e., through a dipping-trough) of the chemical agent. The packaging material 102 may typically comprise a layered structure of one or more internal coating and sealing layers (of, e.g., polyethylene), a metal foil (such as aluminum foil), a laminating layer (or paper layer) and an external layer (of, e.g., polyethylene), in accordance with conventional practice.

Excess chemical agent solution may be removed by rollers 110 or other such means, e.g., an air knife, and the packaging material may be subsequently formed into a longitudinally sealed tube by a longitudinal sealing apparatus 112. In the event a lap seal (as opposed to a fin seal) is desired, a strip 108 may be applied to one edge of the packaging material to reinforce the longitudinal seam, and to prevent the product from coming into contact with the edge of the packaging material 102. Application of such strips is known in the art.

Figure 4:
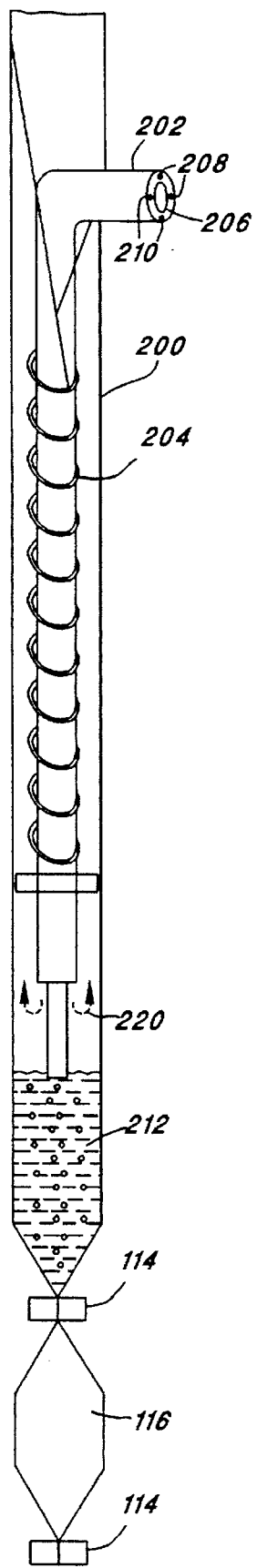
FIG. 4 is a partial perspective view of the aseptic packaging apparatus of FIG. 3 showing a high intensity incoherent pulsed light filling and sterilization assembly.

An important aspect of the aseptic packaging apparatus 38 is a pulsed light filling and sterilization assembly 200 (or product filling and flashlamp assembly), shown in more detail in FIG. 4. The illustrated assembly 200 comprises an outer support tube 202, having attached thereto one or more flashlamps 204 distributed about and along the tube 202 such that upon pulsing, the entire inner surface of the longitudinally sealed tube of packaging material is subjected to a series (e.g., four) of intense (i.e., 0.01 to 50 J/cm$^2$, e.g., 0.5 J/cm$^2$, energy density measured at the surface of the packaging material), short duration (i.e., from 0.001 to 100 milliseconds, e.g., 0.3 milliseconds), broad-spectrum (e.g., 170 to 2600 nm; $1.8 \times 10^{15}$ Hz to $1.2 \times 10^{14}$ Hz) incoherent pulses of light.

Note that the light may also include continuous wave and monochromatic or polychromatic light having wavelengths outside the broad spectrum. However, at least 60%, preferably at least 70%, of the energy of the light should be from light having wavelengths within the broad spectrum defined above.

The light impinges upon the inner surface of the longitudinally sealed tube of packaging material, so as to deactivate organisms substantially at (i.e., within one millimeter of) the surface of the packaging material. Such exposure, in combination with the chemical agent, deactivates, i.e., kills or sterilizes, substantially all (i.e., more than 50%, e.g., 90%) of the organisms on the surface of the packaging material.

A variety of arrangements of the flashlamps along the support tube 202 are contemplated, the essential feature being that the entire inner surface of the longitudinally sealed tube of packaging material is exposed to the pulsed light.

Within the support tube 202 is a sterile food product tube 206. Sterile food product 212 is fed into the longitudinally sealed tube of packaging material via the sterile food product tube 206. The sterile food product 212 can be produced by a variety of known techniques, including the use of light pulses as described in the '559 patent, or may be produced using a combination of intense incoherent light pulses, and preheating and/or treatment with a chemical agent (which may or may not be the same chemical agent as is used to treat the packaging material), as described herein. A flashlamp electrical cable 208 and optional lamp coolant lines 210 may be located intermediate the support tube 202, and the sterile food product tube 206. In addition, sterile air provided under pressure from a suitable supply (not shown) may be conducted for discharge within the longitudinally sealed tube of packaging material. Sterile air may be produced by a variety of techniques, e.g., filtration or incineration, including the use of intense incoherent light pulses as described in the '559 patent.

In operation, after the longitudinally sealed tube of packaging material, which is transversely sealed by a suitable transverse sealing apparatus 114, has received a predetermined portion of sterile food product 212, the longitudinally sealed tube of packaging material is advanced one "package length", while the flashlamp assembly is pulsed a plurality of times in order to repeatedly sterilize, i.e., deactivate organisms on, the entire adjacent interior of the longitudinally sealed tube of packaging material above the sterile food product 212. Sterile air 220 exits the support tube 202 and is carried over the flashlamp assemblies to cool the flashlamps, to remove from the longitudinally sealed packaging material tube any ablation products produced by the flashlamp discharge and to prevent contamination from settling on the treated area. Following transverse sealing, the packages may be separated into individual consumer packages 116.

Figure 5:
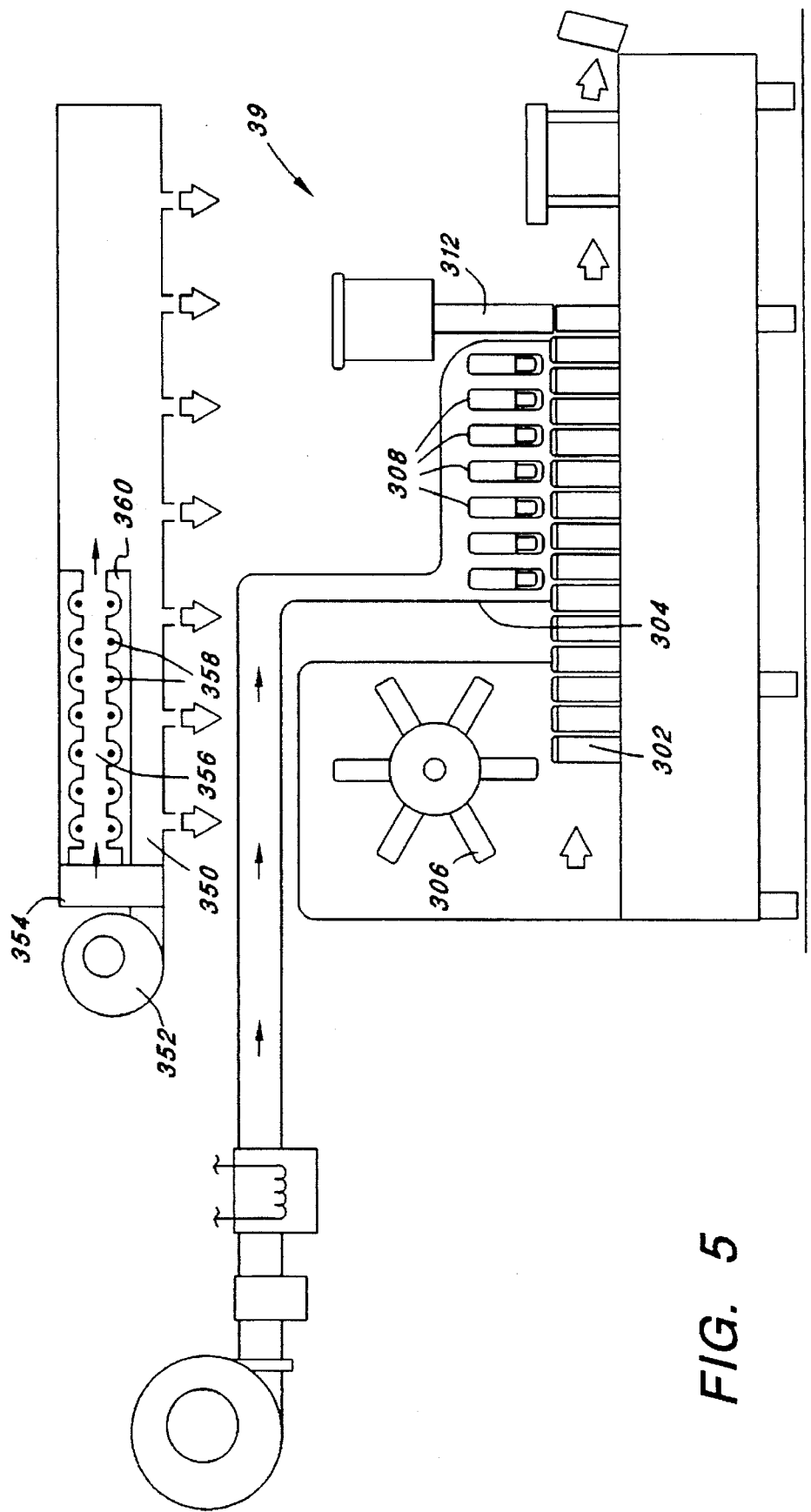
FIG. 5 is a detailed perspective view of a second type of aseptic packaging apparatus that includes another embodiment of the pulsed light treatment system of FIG. 2 employing chemical synergy.

The present method may also be applied to other types of aseptic packaging systems, such as those which utilize preformed produce containers. In this regard, illustrated in FIG. 5 is an aseptic packaging apparatus 39. The packaging apparatus 38 utilizes preformed produce containers 302 which are introduced into a sterilization zone 304 of the packaging apparatus 38. The chemical agent, as previously described, may be sprayed into containers 302 by means of spraying apparatus 306. Subsequently, the containers 302 pass through a series of flashlamp treatment stations 308 in which reciprocating "U" shaped flashlamps, linear flashlamps, bulb type flashlamps and/or flashlamps of other configurations are introduced above or into the container openings and pulsed at least once per container 302. The series of treatment stations is then withdrawn and the containers are advanced by one station, as the process is repeated so that the entire interior surface of each of the containers is subjected to a plurality of intense incoherent light pulses as it progresses along the series of treatment stations 308. A sterile air purge apparatus may be utilized to remove any material ablated from the interior of the containers, to prevent contamination from settling in the treated containers, and to cool the flashlamps. A stationary battery of flashlamps may also be provided to treat the exterior and edge surfaces of the containers upon their passage through the flashlamp treatment zone. The containers, having been sterilized, subsequently pass through a filing station 312 where a food product is introduced into each of the containers, which are subsequently sealed at the top by a sterile lid.

A laminar flow of sterile air may be provided over the entire aseptic packaging apparatus 39 in order to prevent the infection of the containers. The sterile air may be provided by a gas sterilization apparatus 350 that includes an air input blower 352, which pumps air through a filter 354 to a pulsed light treatment zone 356 containing a bank of high power Xenon flashlamps 358 enclosed in a reflective housing 360. The sterile air is continuously forced through the treatment zone 356 at a rate that, in conjunction with the pulse rate of the lamps 358, insures that all of the sterile air is subjected to a plurality of high intensity polychromatic incoherent light pulses, as previously described, as it passes through the treatment zone 356. Desirably, the light pulses will be a UV-rich (i.e., having at least 5 percent of its light energy at wavelengths shorter than 300 nm) and will desirably have an energy density of at least 0.5 joule per square centimeter throughout the treatment zone through which all of the sterile air passes. The pulse duration may typically be in the range of from about 0.001 to 100 milliseconds, e.g., 0.3 milliseconds.

A multiple-lamp reflector array provides multidirectional, substantially even illumination to the air or other gas flowing therethrough, so that a dust particle or bacterial colony forming organism is treated from all sides and is not self-shielded.

Figure 6:
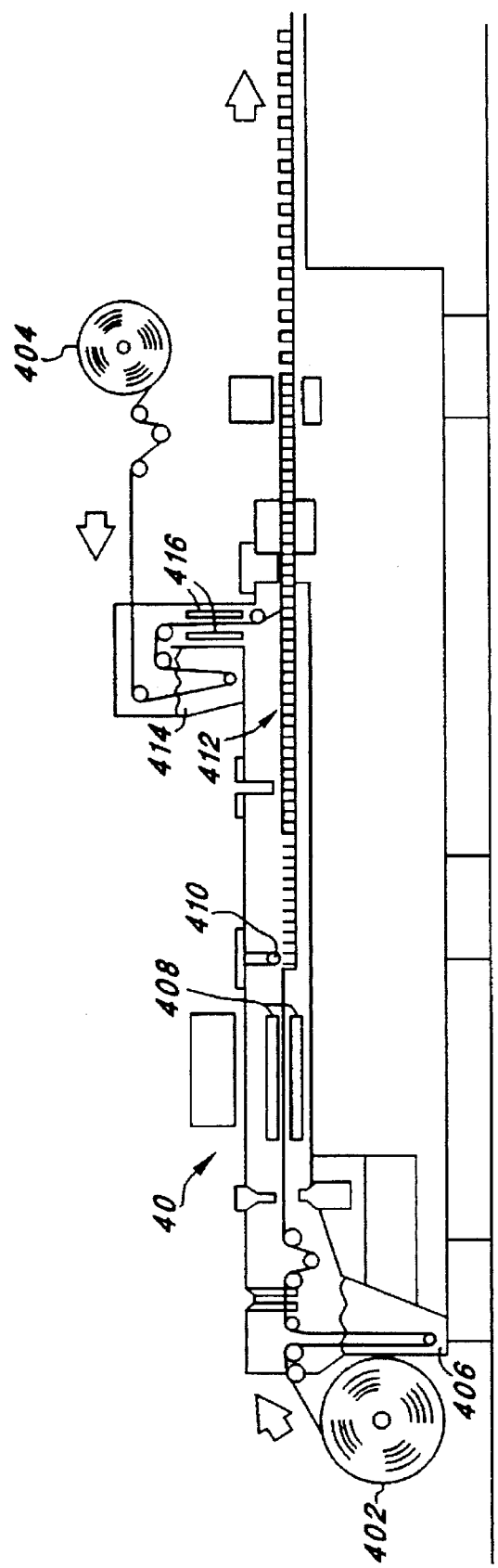
FIG. 6 is a detailed perspective view of a third type of aseptic packaging apparatus that includes another embodiment of the pulsed light treatment system of FIG. 2 employing chemical synergy.

Illustrated in FIG. 6 is an additional embodiment of an aseptic packaging apparatus 40 which comprises two rolls or reels 402, 404 of packaging material, one for the container body of the finished packages and one for package lids. The material for the container body is conducted through a reservoir 406 of the chemical agent, as previously described. The packaging material 402 for the container body is conducted through a suction and drier section to remove excess chemical agent, and is subsequently subjected to intense incoherent light pulses by an array 408 of flashlamps extending longitudinally along the direction of travel of the packaging material 402. After being subjected to the intense incoherent light pulses, the packaging material 402 is thermoformed into suitable containers by a forming apparatus 410. The containers are then filled with an aseptically processed food product or foodstuff at a filling station 412. The packaging material for the lid is also passed through a chemical agent bath 414, is subjected to a plurality of intense incoherent light pulses by a flashlamp array 416 and is utilized to seal the filled, formed containers. The entire apparatus is maintained under sterile air blanket similar to that described above.

Referring to FIG. 7, a schematic diagram is shown of a pulsed light treatment system 10 employing thermal synergy to achieve an improved organism deactivation rate substantially at a surface 12 of a food product 14. In practice, a food product 14, such as the food product 14 described in reference to FIG. 1, is passed through a heat treatment zone. A suitable conveyor (not shown), such as a conveyor belt, can be used to convey the food product 14.

Within the heat treatment zone, warm or hot water is used to spray the food product 14. The water is stored in a reservoir 702, from which it passes via a suitable conduit, such as a pipe. Heaters 704 heat the water within the reservoir (making it warm or hot water), and in response to the opening of a valve (not shown), the hot or warm water flows from the reservoir via a suitable Conduit, such as a pipe, to one or more nozzles 700, 701. Such heaters 704 and reservoirs 702, e.g., water heaters, are well known in the art, and the nozzles 700, 701 can be any type of nozzle suitable for spraying the surface of the food product. The warm or hot water is heated to a temperature of at least 20° C., e.g., to between 30° C. and 90° C., preferably about 70° C., by the heaters 704. As a result of the water being sprayed over the surface 12 of the food product 14, the surface 12 of the food product 14 is heated to approximately the temperature of the water. Such heating in, e.g., beef carcasses is evidenced by a whitening of the surface of the carcass. The natural color of the carcass does however return in the event the carcass is recooled.

Note that in addition to heating the surface of the food product 14, the warm or hot water may interact chemically with organisms on the surface 12 of the food product 14. As a result, both thermal and chemical synergy may assist in the killing of organisms on the surface 12 of the food product 14 in this embodiment.

Note further that the temperature to which the food product 14 is preferably heated depends on the nature of the food product 14 and the type of organisms to be deactivated. Note, however, that the temperature to which the food product is heated need not be sufficient to deactivate organisms. For example, meats, such as beef carcasses, can be heated using warm or hot water that has a temperature of about 70° C., which is insufficient to deactivate some types of organisms, and, advantageously, does not result in a changed flavor or changed coloration in the meat.

After being heated by the warm or hot water, the food product 14, is passed into a pulsed light treatment zone, wherein it is exposed to intense, short duration, broad spectrum, polychromatic light pulses 28, as described above. The light pulses 28, in combination with the heating of the food product, using warm or hot water or other heating means, such as ovens or heaters, cause an improved deactivation rate with respect to organisms at or near the surface of the food product 14.

Figure 8A:
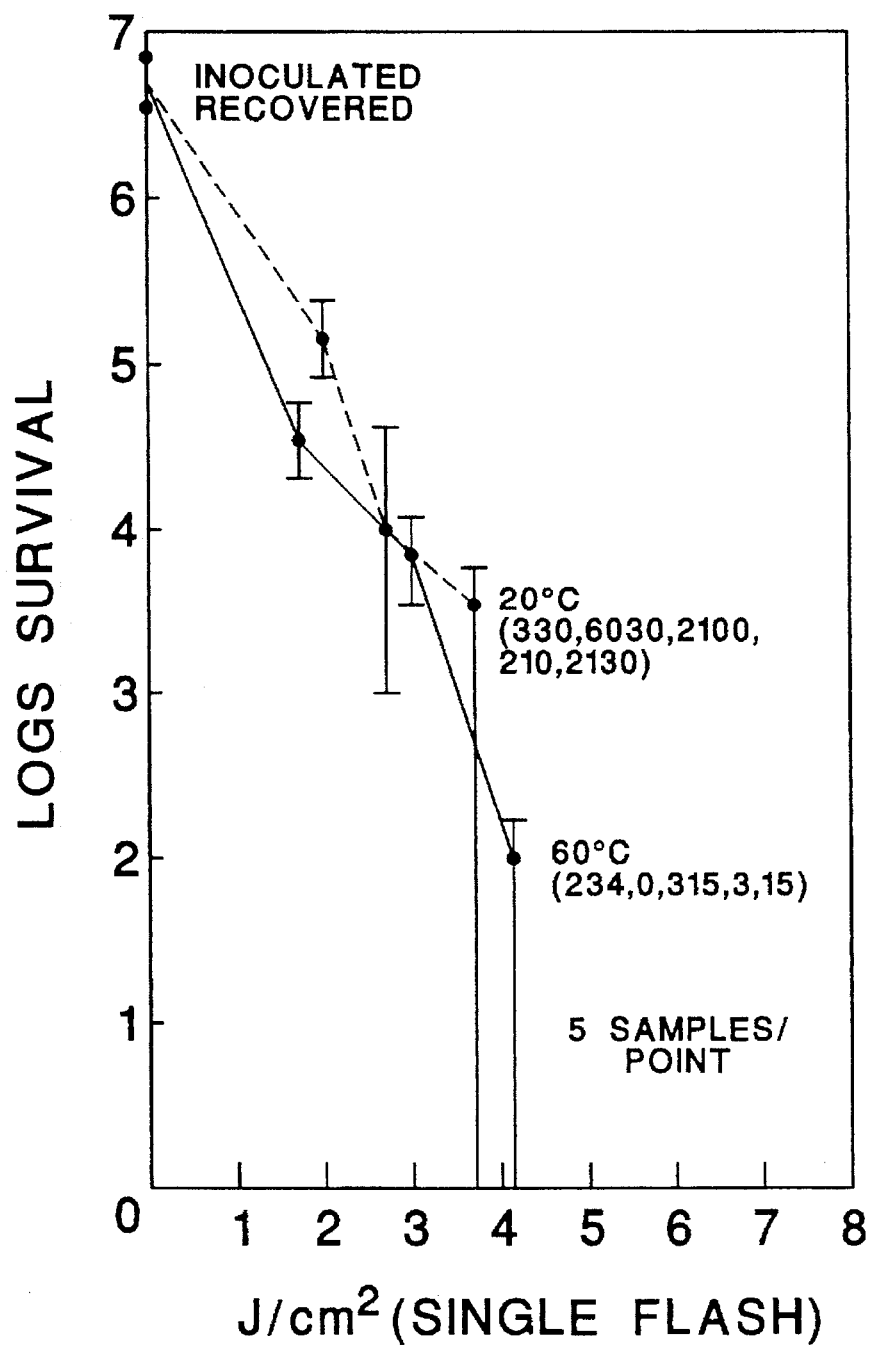
FIG. 8A is a graph showing results of a demonstration test of the pulsed light treatment system of FIG. 8 using *Bacillus subtilis* spores treated with heat and one flash of intense, short duration, broad spectrum polychromatic light.

Referring to FIG. 8, a schematic diagram is shown of a pulsed light treatment system 80 employing thermal synergy to achieve an improved organism deactivation rate substantially at a surface of (i.e., within 1 millimeter of) a packaging material 35. A roll or reel 36 of the packaging material 35 is shown. The packaging material 35 can be a laminated packaging material, as described above. In practice, the packaging material 35 is rolled off of the roll 36 through rollers 37 (or other mechanical guides) to a heat treatment zone, as described above. Within the heat treatment zone, heaters 800 are used to heat the packaging material 35 at its inner and/or outer surfaces (or either of the inner or outer surfaces, as described), and/or to heat the atmosphere, e.g., air, surrounding (or adjacent to) the packaging material 35. Preferably the packaging material 35 and/or atmosphere surrounding (or adjacent to) the packaging material 35 are heated to a temperature of at least 20° C., e.g., 80° C. Such heaters 800, which may be resistive heating elements, are well known in the art.

After being heated (and/or having the atmosphere around it heated) in the heat treatment zone, the packaging material 35 is passed through rollers 37 (or other mechanical guides) to a pulsed light treatment zone, as described above. Within the pulsed light treatment zone, lamps 32 are used to generate high intensity polychromatic light pulses 28, which are applied to the packaging material 35. The combination of the heating by the heaters 800 and the application of high intensity polychromatic light 28 by the lamps 32 results in an improved deactivation rate for organisms residing at or near the surface of the packaging material 35.

Note that the heat treatment zone and the pulse light treatment zone, may, in one embodiment, be combined in a single physical area. Within the single physical area, the heaters 800 may first increase the temperature of the packaging material 35 and/or atmosphere around the packaging material 35 and the flashlamps 32 may then apply the intense, short duration pulses of broad spectrum, polychromatic light 28.

The apparatus 80 shown in FIG. 8 is analogous to the apparatus 34 shown in FIG. 2, except that the apparatus 80 of FIG. 8 employs thermal synergy, as opposed to chemical synergy. Note however that the apparatuses 34, 80 of FIGS. 2 and 8 can easily be combined by passing the packaging material 35 through both the chemical spray zone and the heat treatment zone before the application of the pulsed light treatment. (Such combination can also be made of the apparatuses in FIGS. 1 and 7 for treating the food product 14). Depending on the application of the present invention, i.e., the organisms to be deactivated and the type of packaging material 35, the packaging material 35 can be first passed through the heat treatment zone or the chemical spray zone, and then passed through the other of theses two zones before being passed through the pulsed light treatment zone. In addition, the chemical spray zone and/or the heat treatment zone may be combined with the pulsed light treatment Zone in a single physical area.

Demonstration of thermal synergy is made placing a 10 μl droplet containing $7.1 \times 10^6$ spore colony forming units of *Bacillus pumilus* ATCC 27142 spores onto a surface of each of two polypropylene desert cups, such as those commonly used in the art of food packaging. The inoculum is allowed to dry (for about one hour). Next, one of the polypropylene desert cups is treated at about 20° C. with an intense, short duration pulse of broad spectrum polychromatic light. The intensity of the pulse of light is 2 $J/cm^2$ and its duration is 0.3 mS. The second of the polypropylene desert cups, and an air atmosphere surrounding the second desert cup are heated for about five minutes, using heaters (such as those shown in FIG. 8), to a temperature of about 60° C. The second desert cup is then exposed to intense, short duration pulse of broad spectrum polychromatic light.

Each of the two polypropylene desert cups are next swabbed using a wet cotton swab (having been dipped in sterile water). Each wet swab is then placed into a test tube containing 3 ml of phosphate buffer, and broken off below the portion of the swab that has been handled. Next a dry swab is used to swab each of the polypropylene desert cups, and is also broken off into one of the test tubes. The test tubes are shaken to recover the spores from the swabs into the buffer. The buffer is sampled and plated onto standard plate count agar (SPCA) plates, and standard microbiological techniques are used to determine the logs of organisms still surviving. These quantities are compared to determine the difference in logs of organisms on the two desert cups, i.e., the increase in deactivation achieved by the combination of thermal treatment at 60° C. and the pulsed light treatment, over the deactivation achieved by the pulsed light treatment at 20° C.

Additional demonstrations are carried out as described above using light pulses having intensities of 3 and 4 $J/cm^2$. Results from exemplary demonstrations are shown graphically in FIG. 8A. Thus, it is shown that the application of heat in combination with the intense, short duration, broad spectrum, polychromatic light pulse results in increased deactivation of organisms residing at or near the surface of a packaging material.

Figure 9:
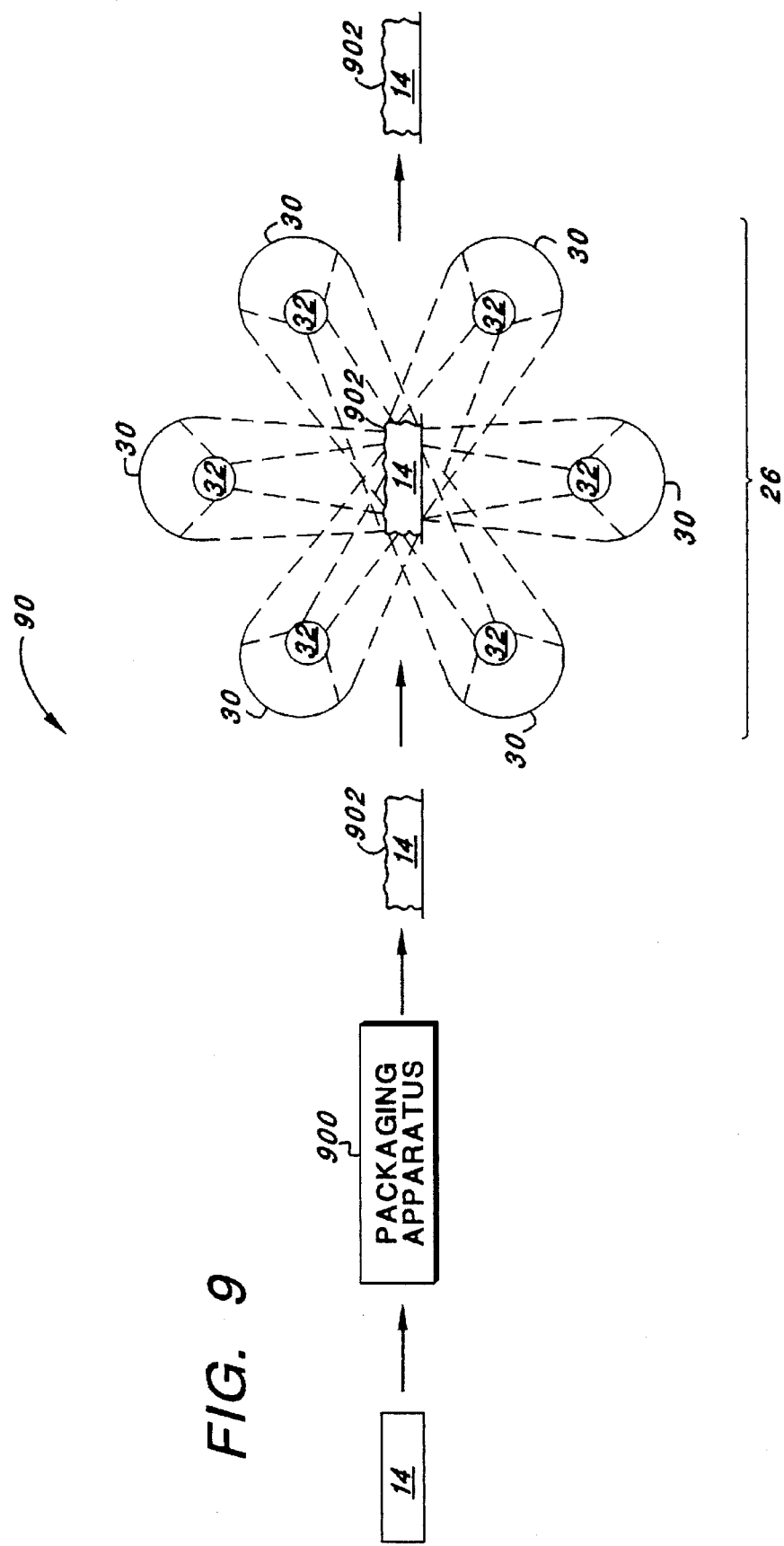
FIG. 9 is a schematic diagram of a pulsed light treatment system employing modified atmosphere packaging synergy to achieve an improved organism deactivation rate substantially at a surface of the food product, as well as increased merchantability of the food product.

Referring to FIG. 9, a schematic diagram is shown of a pulsed light treatment system 90 employing modified atmosphere packaging synergy to achieve an improved organism deactivation rate substantially at a surface 12 of the food product 14, as well as increased merchantability of the food product 14. In operation, the food product 14, such as beef steak, is passed through a packaging apparatus 900 wherein the food product is sealed in a modified atmosphere package 902. The packaging apparatus 900 can be any type of packaging apparatus that seals the food product 14 within a volume designed to contain a modified atmosphere. The modified atmosphere may be fully or partially evacuated, or pressurized; and/or may contain a chemical agent, such as a gas, liquid, liquid solution, gelatin, or the like. As an example, the modified atmosphere may include an elevated oxygen content, such as an oxygen content greater that atmospheric, i.e., greater than the concentration found in air, or such as a >65% oxygen content.

After the food product 14 is sealed within the modified atmosphere package 902, it is passed into a pulsed light treatment zone wherein it is exposed to intense, short duration, broad spectrum, polychromatic light pulses 28. The light pulses 28 pass through the modified atmosphere package 902, which must allow light within a prescribed frequency range within the above-defined broad spectrum to pass through without excessive attenuation. Excessive attenuation occurs, for example if, in order to pass sufficient light energy through the modified atmosphere package 902 to effect deactivation of organisms at the surface of the food product, the polychromatic light impinging upon the surface of the modified atmosphere package 902 has to be of such great intensity that it causes the modified atmosphere package 902 to melt, burn or ablate.

As a result of the modified atmosphere package 902 being exposed to the pulses of light 28, organisms at or near the surface of the food product 14, i.e., within one millimeter of the surface of the food product 14, are deactivated. Furthermore, various other advantageous effects occur. For example, increased deactivation of organisms may occur when chemicals such as those described above are included in the modified atmosphere, or when a modified atmosphere evolves after the food product 14 is sealed within the modified atmosphere package 902. As a further example, in a preferred application wherein the food product is beef meat and the modified atmosphere package 902 contains higher concentrations of oxygen ($O_2$) than atmospheric, e.g., >65% $O_2$ concentration, prolongation of the food product's red color is achieved. Because beef meat is prone to relatively quick discoloration when packaged using heretofore known techniques, this benefit is particularly advantageous. As a result of such prolongation of the beef meat'as color, the food product 14 remains marketable for an extended period of time.

Note that the modified atmosphere package 902 need not contain a modified atmosphere at the time the food product 14 is sealed within the modified atmosphere package 902. Instead the modified atmosphere may evolve as a result of, e.g., chemical reactions that occur within the modified atmosphere package 902 after being sealed. The evolution of the modified atmosphere may or may not occur as a result of the food product 14 and/or modified atmosphere package 902 being exposed to the light pulses. The modified atmosphere, in some embodiments, can be characterized as a chemical treatment of the food product 14, and modified atmosphere packaging can, in such embodiments, be described as applying a chemical agent to the food product 14. Such is the case, for example, when one of the chemical agents described above are included in the modified atmosphere, or when chemical reactions occurring after the food product 14 is packaged, result in the modified atmosphere. Thus, modified atmosphere packaging synergy can, in some embodiments, be accurately described as a form of chemical synergy, which is described in reference to FIG. 1. As with the chemical synergy described in FIG. 1, modified atmosphere packaging, may advantageously be combined with thermal synergy to achieved an increased deactivation rate, and potentially prolongation of the period during which the food product remains merchantable.

While the invention herein disclosed has been described by means of specific embodiments and applications thereof, numerous modifications and variations could be made thereto by those skilled in the art without departing from the scope of the invention set forth in the claims.

What is claimed is:

1. A method for deactivating contaminants, including at least one contaminant from a group of contaminants consisting of biological contaminants and chemical contaminants, substantially at a titanium dioxide supplemented surface of a packaging material comprising:

illuminating the titanium dioxide supplemented surface of the packaging material with light having frequencies within a first prescribed frequency range, at least a portion of the light deactivating contaminants substantially at the titanium dioxide supplemented surface of the packaging material;

illuminating the titanium dioxide supplemented surface of the packaging material with light having frequencies within a second prescribed frequency range, at least a portion of the light initiating the release of a highly reactive agent in a reaction in which titanium dioxide serves as a catalyst, the highly reactive agent also deactivating contaminants substantially at the titanium dioxide supplemented surface of the packaging material;

whereby improved deactivation of contaminants substantially at the titanium dioxide supplemented surface of the packaging material is achieved.

2. The method of claim 1 wherein said illuminating of said titanium dioxide supplemented surface with light having frequencies within said first prescribed frequency range includes illuminating said titanium dioxide supplemented surface with light having frequencies in the range of 200 nm to 320 nm.

3. The method of claim 1 wherein said illuminating of said titanium dioxide supplemented surface with light having frequencies within said second prescribed frequency range includes illuminating said titanium dioxide supplemented surface with light having frequencies in the range of 300 nm to 415 nm.

4. The method of claim 3 wherein said illuminating of said titanium dioxide supplemented surface with light having frequencies within said first prescribed frequency range includes illuminating said titanium dioxide supplemented surface with light having frequencies in the range of 200 nm to 320 nm.

5. The method of claim 4 wherein said illuminating of said titanium dioxide supplemented surface with light having frequencies within said second prescribed frequency range includes illuminating said titanium dioxide supplemented surface with light having frequencies within said second prescribed frequency range simultaneously with said illuminating of said titanium dioxide supplemented surface with light having frequencies within said first prescribed frequency range.

6. The method of claim 5 wherein:

said illuminating of said titanium dioxide supplemented surface with light having frequencies within said first prescribed frequency range includes illuminating said titanium dioxide supplemented surface with light having frequencies within said first prescribed frequency range using a lamp; and said illuminating of said titanium dioxide supplemented surface with light having frequencies within said second prescribed frequency range includes illuminating said titanium dioxide supplemented surface with light having frequencies within said second prescribed frequency range using the lamp.

7. The method of claim 6 wherein:

said illuminating of said titanium dioxide supplemented surface with light having frequencies within said first prescribed frequency range includes illuminating said titanium dioxide supplemented surface with light having an intensity of from between 0.01 to 50 $J/cm^2$; and said illuminating of said titanium dioxide supplemented surface with light having frequencies within said second prescribed frequency range includes illuminating said titanium dioxide supplemented surface with the light having an intensity of from between 0.01 to 50 $J/cm^2$.

8. The method of claim 6 wherein:

said illuminating of said titanium dioxide supplemented surface with light having frequencies within said first prescribed frequency range includes illuminating said titanium dioxide supplemented surface with a pulse of light having a duration of from 0.001 to 100 milliseconds; and said illuminating of said titanium dioxide supplemented surface with light having frequencies within said second prescribed frequency range includes illuminating said titanium dioxide supplemented surface with the pulse of light.

9. The method of claim 8 wherein:

said illuminating of said titanium dioxide supplemented surface with light having frequencies within said first prescribed frequency range includes illuminating said titanium dioxide supplemented surface with three additional pulses of light each having a duration of from 0.001 to 100 milliseconds; and said illuminating of said titanium dioxide supplemented surface with light having frequencies within said second prescribed frequency range includes illuminating said titanium dioxide supplemented surface with the three additional pulses of light.

10. The method of claim 1 wherein said illuminating of said titanium dioxide supplemented surface with light having frequencies within said second prescribed frequency range includes illuminating said titanium dioxide supplemented surface using light that passes through said packaging material before reaching said titanium dioxide supplemented surface, said packaging material being at least partially transparent to said light having frequencies within said second prescribed frequency range.

11. A method for deactivating one or more contaminants, including at least one contaminant from a group of contaminants consisting of biological contaminants and chemical contaminants, within a treatment cell comprising:

illuminating, within the treatment cell, one portion of the one or more contaminants with light having frequencies within a first prescribed frequency range, at least a portion of the light having frequencies within the first prescribed frequency range deactivating the one portion of the one or more contaminants;

illuminating, within the treatment cell, another portion of the one or more contaminants with light having frequencies within a second prescribed frequency range, said another portion being at a titanium dioxide supplemented surface, at least a portion of the light having frequencies within the second prescribed frequency range initiating the release of a highly reactive agent in a reaction in which titanium dioxide serves as a catalyst, the highly reactive agent deactivating said another portion of the one or more contaminants;

whereby improved deactivation of the one or more contaminants is achieved.

12. The method of claim 11 wherein said illuminating with light having frequencies within said second prescribed frequency range includes illuminating with light having frequencies in the range of 300 nm to 415 nm.

13. The method of claim 12 wherein said illuminating with light having frequencies within said first prescribed frequency range includes illuminating with light having frequencies in the range of 200 nm to 320 nm.

14. The method of claim 13 wherein said illuminating with light having frequencies within said second prescribed frequency range includes illuminating with light having frequencies within said second prescribed frequency range simultaneously with said illuminating with light having frequencies within said first prescribed frequency range.

15. The method of claim 14 wherein:

said illuminating with light having frequencies within said first prescribed frequency range includes illuminating with light having frequencies within said first prescribed frequency range using a lamp; and said illuminating with light having frequencies within said second prescribed frequency range includes illuminating with light having frequencies within said second prescribed frequency range using the lamp.

16. The method of claim 15 wherein:

said illuminating with light having frequencies within said first prescribed frequency range includes illuminating with light having an intensity of from between 0.01 to 50 $J/cm^2$; and said illuminating with light having frequencies within said second prescribed frequency range includes illuminating with the light having an intensity of from between 0.01 to 50 $J/cm^2$.

17. The method of claim 16 wherein:

said illuminating with light having frequencies within said first prescribed frequency range includes illuminating with a pulse of light having a duration of from 0.001 to 100 milliseconds; and said illuminating with light having frequencies within said second prescribed frequency range includes illuminating with the pulse of light.

18. An apparatus for deactivating one or more contaminants, including at least one contaminant from a group of contaminants consisting of biological contaminants and chemical contaminants comprises:

a treatment cell;

an anatase titanium dioxide supplemented surface within the treatment cell;

a lamp assembly positioned within the treatment cell, the lamp including means for illuminating one portion of the one or more contaminants with light having frequencies within a first prescribed frequency range, at least a portion of the light having frequencies within the first prescribed frequency range deactivating the one portion of the one or more contaminants; and means for illuminating another portion of the one or more contaminants with light having frequencies within a second presoribed frequency range, said another portion being at an anatase titanium dioxide supplemented surface, at least a portion of the light having frequencies within the second prescribed frequency range initiating the release of a highly reactive agent in a reaction in which titanium dioxide serves as a catalyst, the highly reactive agent deactivating said another portion of the one or more contaminants;

whereby improved deactivation of the one or more contaminants is achieved.

19. The apparatus of claim 18 wherein said anatase titanium dioxide supplemented surface is included within a packaging material.

20. The apparatus of claim 18 wherein said lamp assembly includes said means for illuminating said other portion of said one or more contaminants with light having frequencies within said second prescribed frequency range.

21. The apparatus of claim 18 wherein said anatase titanium dioxide supplemented surface includes at least one supplemented surface from a group of supplemented surfaces consisting of a screen mesh, a porus mass, and an interior surface of the treatment cell.

* * * * *